United States Patent
Kakibayashi et al.

[11] Patent Number: 5,866,905
[45] Date of Patent: Feb. 2, 1999

[54] ELECTRON MICROSCOPE

[75] Inventors: Hiroshi Kakibayashi, Nagareyama; Yasuhiro Mitsui, Fuchu; Hideo Todokoro, Nishi-tama-gun; Katsuhiro Kuroda, Hachiouji; Masanari Koguchi, Kodaira; Kazutaka Tsuji, Hachiouji; Tatsuo Makishima, Katsushika-ku; Mikio Ichihashi, Kodaira; Shigeto Isakozawa, Hitachinaka; Ruriko Tsuneta, Kokubunji; Kuniyasu Nakamura, Musashino; Kensuke Sekihara, Musashimurayama; Jun Motoike, Hachiouji, all of Japan

[73] Assignee: Hitachi, Ltd., Tokyo, Japan

[21] Appl. No.: 686,740

[22] Filed: Jul. 26, 1996

Related U.S. Application Data

[63] Continuation-in-part of Ser. No. 398,684, Mar. 6, 1995, Pat. No. 5,552,602, which is a continuation-in-part of Ser. No. 79,273, Jun. 21, 1993, Pat. No. 5,475,218, which is a division of Ser. No. 882,970, May 14, 1992, Pat. No. 5,278,408.

[30] Foreign Application Priority Data

| May 15, 1991 | [JP] | Japan | 3-110126 |
| Dec. 15, 1995 | [JP] | Japan | 7-326817 |
| May 17, 1996 | [JP] | Japan | 8-123064 |

[51] Int. Cl.[6] ............................ H01J 37/26
[52] U.S. Cl. ........................................ 250/311
[58] Field of Search ........................ 250/311, 306, 250/307, 396 R

[56] References Cited

U.S. PATENT DOCUMENTS

| 3,847,689 | 11/1974 | Fletcher et al. | 250/311 |
| 4,038,543 | 7/1977 | Kristh et al. | 250/311 |
| 4,068,123 | 1/1978 | Kokubo | 250/311 |
| 4,099,055 | 7/1978 | Todokoro | 250/311 |
| 4,608,491 | 8/1986 | Kakubo | 250/311 |
| 4,680,469 | 7/1987 | Nomura et al. | 250/311 |
| 4,724,320 | 2/1988 | Ino et al. | 250/310 |
| 4,866,273 | 9/1989 | Kobayashi et al. | 250/311 |
| 4,942,299 | 7/1990 | Kazinerski | 250/307 |
| 4,945,237 | 7/1990 | Shii et al. | 250/311 |
| 4,975,578 | 12/1990 | Tomimasu et al. | 250/397 |
| 5,095,207 | 3/1992 | Tong | 250/306 |
| 5,144,148 | 9/1992 | Eigler | 250/492.2 |
| 5,278,408 | 1/1994 | Kakibayashi | 250/311 |
| 5,650,621 | 7/1997 | Tsuneta et al. | 250/311 |

FOREIGN PATENT DOCUMENTS

| 0348992 | 1/1990 | European Pat. Off. |
| 0472235A1 | 2/1992 | European Pat. Off. |
| 62-096807 | 10/1985 | Japan |
| 61-78041 | 4/1986 | Japan |
| 1211849 | 11/1989 | Japan |

OTHER PUBLICATIONS

Mayer et al, "Structures of Nb/$Al_2O_3$ Interfaces Produced by Different Experimental Routes", *Materials Research Society*, vol. 183, pp. 55–58, no dated.

U. Gross et al, "The Microprocessor–Controlled CM12/STEM Scanning–Transmission Electron Microscope", *Philips Technical Review*, Nov. 1987, vol. 43, No. 10, Eindhoven, The Netherlands.

M. Haider, "Filtered Dark–Field and Pure Z–Contrast: Two Novel Imaging Modes in a Scanning Transmission Electron Microscope", 1989, North–Holland, Amsterdam.

*Fiber Optically Coupled TV Screen*, Model 622SC.

*Primary Examiner*—Kiet T. Nguyen
*Attorney, Agent, or Firm*—Antonelli, Terry, Stout & Kraus, LLP

[57] ABSTRACT

A scanning transmission electron microscope including an electron detection system having a scattering angle limiting aperture (for the inner angle) and a scattering angle limiting aperture (for the outer angle) between a specimen and an electron detector (comprising a scintillator and a light guide) and only one electron detector is installed.

12 Claims, 25 Drawing Sheets

| DETECTOR TYPE | FIRST QUANTUM EFFICIENCY | MULTIPLICATION FACTOR | RELATIVE SENSITIVITY | S/N |
|---|---|---|---|---|
| PHOTOMULTIPLIER | 0.2 | $10^5$ | HIGH | POOR |
| CONVENTIONAL PHOTO-CONDUCTION TYPE IMAGING DEVICE | 0.4 | 1 | LOW | GOOD |
| AVALANCHE-TYPE IMAGING DEVICE | 1.0 | $10^3$ | HIGH | GOOD |

FIG. 11(a)
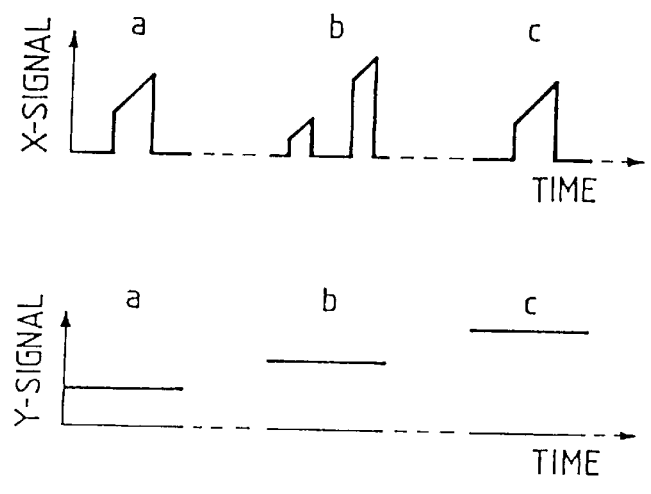
FIG. 11(b)
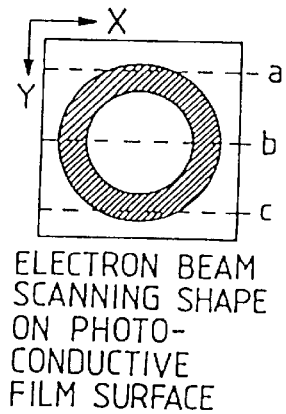
ELECTRON BEAM
SCANNING SHAPE
ON PHOTO-
CONDUCTIVE
FILM SURFACE
FIG. 12
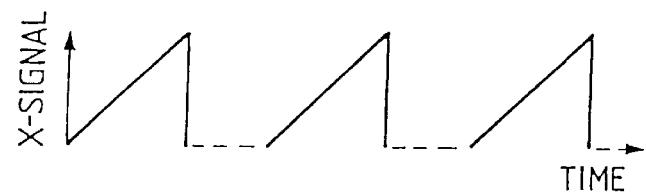
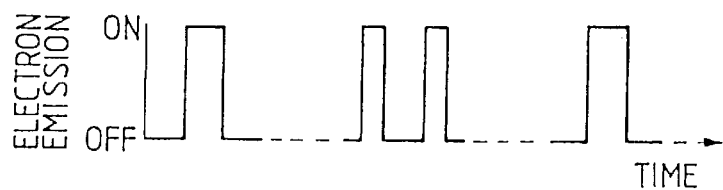

ELECTRON MICROSCOPE

CROSS REFERENCE TO RELATED APPLICATION

This application is a continuation-in-part of application Ser. No. 08/398,684 filed on Mar. 6, 1995, now U.S. Pat. No. 5,552,602, which is a continuation-in-part of application Ser. No. 08/079,273 filed on Jun. 21, 1993, now U.S. Pat. No. 5,475,218, which is a divisional of application Ser. No. 07/882,970 filed on May 14, 1992, now U.S. Pat. No. 5,278,408. The disclosure of application Ser. Nos. 08/398, 684, 08/079,273 and 07/882,970 are hereby incorporated by reference.

BACKGROUND OF THE INVENTION

The present invention relates to an electron microscope for the observation of point defects, impure atoms and their clusters which exist at joint interfaces and contacts in an integrated device formed into a layered structure such as a memory or fast-calculation device.

The present invention also relates to an electron detection instrument for an electron microscope, especially for the purpose described above. More particularly, it concerns an electron detection instrument for observing an electron microscope image corresponding to a specific atomic configuration or crystal structure of a specimen by way of measuring scattered, diffracted, refracted, or transmitted electrons through a specimen at a high sensitivity and a high signal-to-noise ratio in a desired range of detection angle.

As described in Proc. Mat. Res. Soc. Symp. Vol. 183 (Materials Research Society, San Francisco, 1990) p. 55, the conventional electron microscope can be used for inferring a 3-dimensional atomic arrangement from several electron microscope images observed from different directions. In addition, a technique for obtaining a 2-dimensional image of a 3-dimensional atomic structure is disclosed in Japanese Patent Laid-open No. 61-78041.

On the other hand, a prior electron detection instrument for an electron microscope is constructed as shown in FIG. 18, disclosed in the "Ultramicroscopy," 28, (1989), 240. In the figure, the electron detection instrument is placed in an STEM (scanning transmission electron microscope). The STEM comprises an electron gun 20, illumination lenses 21, electron deflector coils 22, and objective lenses 23. The electron detection instrument comprises an electron-photon converting scintillator 31, light guides 32, photomultipliers 33, and a monitor 34. There are provided two separate electron detection instruments for use of different detected electrons. One electron detection instrument is for observing a dark-field image only with electrons scattered at a high angle, having an annular scintillator 31a. The other electron detection instrument is for observing a bright-field image only with transmitted electrons at a low angle, having a circular scintillator 31b. In operation, the scintillator 31 detects electrons from the specimen, and then converts these electrons to photons. These photons are fed to the photomultiplier. A signal output of the photomultiplier 33 corresponds to intensity of the electrons. The output signal is synchronized with scanning the incident electron beam by a scanning circuit 25 before being brightness-modulated and displayed on the monitor 34. The monitor 34 shows an electron microscope image.

A prior imaging instrument for electron microscope is constructed as shown in FIG. 19, the instrument being described in the "Instruction Manual Model 622SC Fiber Optically Coupled TV System," 1991, Gatan Inc., 6678 Owens, Dr, Pleasanton, Calif. 94588. To pick up an electron microscope image, the imaging instrument is placed on a flange provided at a bottom of a camera chamber 28 of the electron microscope. The imaging instrument comprises an electron-photon converting scintillator 41, optical fiber plates 42, an image intensifier 43, a prior photoconduction-type imaging device 44, an imaging device control system 45, and a monitor 34. One optical fiber plate 42 is placed between the scintillator 41 and image intensifier 43 and the other optical fiber plate 42 between the image intensifier 43 and the photoconduction-type imaging device 44, the both being faced with each other to couple. The prior photoconduction-type imaging device 44 was a imaging tube (representative trade name: Newbicon) having $Zn_{1-x}Cd_xTe$ used for a photoconduction face thereof or a imaging tube (representative trade name: SIT tube) having Si used for a photoconduction face thereof. The quantum effect of both imaging tubes 44 become maximum at a light wavelength of 500 to 750 nm. To make a highly sensitive imaging, the scintillator 41 used for converting an electron image to optical image was the one disclosed in, for example, "Electron Microscopy," Japanese Society of Electron Microscopy, Vol. 27, No. 2, p. 170 (1992). The scintillator 1 has a YAG $(Y_{3-x}Ge_xAl_5O_{12})$ of 550 nm peak luminescence wavelength doped with cerium or GOS $(Gd_2O_2S)$ of 510 nm peak luminescence wavelength doped with praseodymium, cerium, or fluorine.

In FIG. 19, electrons transmitted through specimen (not shown) pass through electron lenses 26, and form an electron microscope image on a fluorescent plate 27, whenever a fluorescent plate 27 closes an opening separating a column 29 and a camera chamber. In operation of the imaging apparatus, at first a fluorescent plate 27 is drawn up from the opening so as to project an electron microscope image onto the scintillator 41.

The scintillator 41 converts electrons to photons. The converted photons are in proportion to intensity of the electron microscope image, or number of the electrons per area. The photons pass the optical fiber plate 42 before coming to the image intensifier 43. The image intensifier 43 converts photons to electrons to magnify more than 100 times before converting the electrons to photons again. The magnified photons pass the optical fiber plate 42 to the photoconductive-film of the photon reception surface of the photoconduction-type imaging device 44 to emit electron-hole pairs. The generated current is detected by an electron beam emitted from an electron gun of the photoconduction-type imaging device 44 to obtain an output signal. The electron beam is scanned at a TV rate of 1/30 sec per screen. As a result, the electron microscope image on the photoconductive-film can be picked up in the same way as an ordinary TV camera.

With the conventional techniques mentioned above, it is necessary to prepare a large number of thinned pieces having a thickness of the order of several nm by cutting a specimen in various directions. In this case, if a target structure in the specimen has an infinitesimal size of the order of nanometers, it is impossible to cut the structure into a plurality of pieces and, thus, impossible to carry out 3-dimensional observation. Even if the target structure is large enough to allow the thinned pieces to be prepared, only part of the target structure is contained in such a piece so that a lot of information is found missing when constructing a 3-dimensional structure based on the electron microscope images of the pieces. In addition, since the observer has to infer a 3-dimensional structure while taking the relation between observation directions and their electron microscope images of thinned pieces, the technique results in very inadequate precision. The accuracy of the observation directions is effected by errors in the angle setting when specimen pieces are cut out and inclinations of the specimen pieces set on the specimen holder of the electron microscope. It is difficult to make the observation conditions by electron microscopes completely uniform for all the specimen pieces. The resulting errors thus give rise to variations in image contrast. An inference image formed by diffracted electrons, or a lattice image, varies depending upon, among other things, the thickness of the specimen and electron diffraction conditions. In addition, even though information on the atomic arrangement can be obtained from a lattice image, it is difficult to identify the atomic species of impurities and point defects.

In addition, it is disclosed in Japanese Patent Laid-open No. 61-78041 that the electron incidence direction to the specimen surface is fixed and all reflected characteristic X-rays generated in the specimen can be obtained by changing the direction of detection. Information on the structure of a 3-dimensional atomic arrangement close to the surface is thereby obtained. Nevertheless, the obtained information is limited to one to two atomic layers on the surface due to the use of all the reflected characteristic X-rays. In addition, since the characteristic X-rays are generated from a region of the micron order, it is impossible to obtain high resolution at an atomic level. It is thus extremely difficult to obtain a 3-dimensional atomic arrangement in the bulk with a high resolution at an atomic level.

On the other hand, the prior electron detection instrument described above has the fixed shape of the detector. For the annular detector shown in FIG. 18, for example, an angle range of electron detection of $q_1$ to $q_2$ is determined in terms of a distance (camera length) between the specimen 24 and the scintillator 31. If an enlarging electron lens is placed between the specimen and the detector, the camera length can be varied. However, the angle range of electron detection changes in proportion to the camera length only. It is therefore impossible to set the angle range of electron detection to a desired one. The sole solution is to take the method that a multiple of detectors having different angle ranges of electron detection are prepared and are replaced depending on an observation object. This solution is expensive and takes too much time and labor for replacement and adjustment to use for practical work.

The prior imaging instrument also has the detectors (e.g. scintillators 31) for transmitted electrons and diffraction pattern provided separately from the one for high-angle scattered electrons. This is disadvantageous in that the detectors can serve only for the respective uses. In particular, the detectors for diffracted pattern must have such a multiple of pixels as a CCD (charge-coupled device) camera. The detector cannot be used in common with the prior ones for transmitted electrons and high angle scattered electrons. This means that a user must unavoidably prepare a plurality of exclusive detectors.

The prior imaging instrument for electron microscope (shown in FIG. 19) has the pixels needed to measure the image. The imaging instrument therefore can detect the scattered, diffracted, refracted, or transmitted electrons through a wide range of angle. However, the electron beam emitted from the electron gun of the imaging device 44 (situated bottom of the imaging device, not shown) is usually scanned in a square area on the surface lying along the lower optical fiber plate 42. The imaging instrument is not used as in the annular detector of the electron detection instrument. The detector therefore cannot detect the electron beam in a desired detection angle range. Also, the prior photoconduction-type imaging device 44 used in the imaging section is too low in sensitivity. Therefore, the image intensifier 43 is necessary to magnify the image intensity. The image intensifier 43, however, generate great amount of quantum noises through its magnification process. This results in terribly bad image quality. Such a phenomenon also occurs in the prior above-described electron detection instrument (shown in FIG. 18) since the photons are magnified by the photomultiplier 33. In particular, the electron detection instrument cannot detect the high-angle scattered electron beam at high signal-to-noise ratio since the beam is too weak. Further, if the scintillator 41 is used for the imaging device 44 having a maximum photon reception sensitivity outside the luminescence wavelength of 500 to 700 nm of the scintillator 41, the sensitivity is lowered.

The scattering angle distribution of the scattered electron intensity emitted from a specimen depends on the atomic number Z of the specimen component element. When a specimen comprises two component elements of high Z and low Z, if the scattering angle of scattered electrons detected by an electron detector is set to $\alpha$ to $\beta$, an electron microscope image in which both elements are contrast-emphasized as an intensity difference of the hatched part can be observed. From comparison of quantitative determination of contrast and contrast calculation using the electron scattering theory, the atomic number Z can be determined, that is, the atomic species can be determined. To execute such an observation, it is necessary that the scattering angle range of scattered electrons detected by the electron detector can be set optionally. When a dark-field detector of a conventional scanning transmission electron microscope is used, the scattering angle range of scattered electrons detected is determined uniquely by the distance (camera length) between a specimen and the detection surface and the inner and outer diameters of an annular scintillator. Therefore, it is impossible to set the scattering angle range of scattered electrons optionally.

According to the prior art, it is described that 3-dimensional coordinates are identified on the basis of a plurality of 2-dimensional images observed in various directions and a 3-dimensional image is reconstructed. However, an actual means for realizing reconstruction of a 3-dimensional image and an artifact reduction method for restructure are not described.

According to the filter correction back projection method which is a conventional 3-dimensional restructure method, if a projection image of a specimen in all directions cannot be obtained in principle, the 3-dimensional structure cannot be reconstructed. However, a projection image of a specimen in all directions cannot be observed by a transmission electron microscope due to restrictions on the equipment constitution thereof and the specimen shape. Therefore, when the 3-dimensional structure of a specimen is reconstructed from a transmission electron microscope image using the conventional 3-dimensional reconstructure method, a problem arises that remarkable artifacts are generated.

SUMMARY OF THE INVENTION

It is a first object of the present invention to obtain a 3-dimensional atomic arrangement and atomic species in the bulk with a high resolution at an atomic level using only a single thin-film specimen and, thus, to allow a 3-dimensional atomic structure to be analyzed accurately in a short period of time.

It is a second object of the present invention to provide an electron detection instrument for electron microscope that can detect an angle distribution of intensity of scattered, diffracted, refracted, or transmitted electrons through a specimen at a high sensitivity and a high signal-to-noise ratio in a desired range of angle.

In order to achieve the first object described above, a system comprising a scanning transmission electron microscope, a specimen goniometer/tilting system, a multi-channel electron detector and a computer was built. The scanning transmission electron microscope includes a unit for radiating an electron beam having a diameter equal to or smaller than the size of one to two atoms. The specimen goniometer/tilting system can be controlled to move a specimen by a distance of the order of nanometers. The multi-channel electron detector allows the range of detection angles of scattered electrons to be arbitrarily set. The computer is used for executing software for controlling the electron microscope and softwares for image processing. The system is thus equipped with facilities for observing a 3-dimensional structure. To speak in more concrete terms, the system is characterized in that some projection images of atomic arrangement are obtained within an angular increment range $\theta$ from a predetermined inclination angle. While rotating the specimen over an angle in a range smaller than the angular increment $\theta$, n images of 2-dimensional atomic-arrangement are produced. Note that within the angular range in which the projection image of atomic arrangement is obtained, the so-called channelling phenomenon must occur at least once. In addition, the angular increment $\theta$ is equal to $\tan^{-1}(d/t)$, where d is the distance from an atom to an adjacent one in the specimen and t is the thickness of the specimen. From the n images of 2-dimensional atomic-arrangement obtained as such, atomic coordinates with rough precision and atomic species are identified. Next, a 2-dimensional atomic-arrangement image is simulated by the informations.

The simulated image is then compared to the 2-dimensional atomic-arrangement images actually measured. Atomic coordinates and atomic species with high accuracy are obtained as both the images match each other. The accurate atomic coordinates and atomic species are used to display a 3-dimensional atomic-arrangement image.

Accordingly, not only is a 3-dimensional atomic arrangement observed, but a structural analysis can also be performed as well using the same system.

A thin-film specimen is observed using the scanning transmission electron microscope using an electron beam with a diameter equal to or smaller than the size of one to two atoms. The observation can result in an atomic-arrangement image. By observing the specimen while varying its inclination by means of the specimen goniometer/tilting system, atomic-arrangement images from various directions can be obtained. By applying image processing to the atomic-arrangement images obtained for various inclination angles, a 3-dimensional atomic arrangement of the specimen can be constructed and atomic species can be identified from an analysis of a relation between the detection-angle ranges of scattered electrons used in the imaging and the degrees of the image contrast.

On the basis of a dislocation between the relative position between two expected characteristic points on an image for the tilt angle when a specimen is tilted around the tilt axis thereof and the relative position actually observed, the effective position of the tilt axis is analyzed. Projection data in the peripheral area where a projection image appears or does not appear depending on the tilt angle is deleted at the stage of preparation.

A plurality of projection images scanned by tilting a specimen are reconstructed 3-dimensionally by using the filter correction back projection method or the algebraic method.

In order to achieve the second object described above, and especially improve the accuracy of 3-dimensional atomic arrangement observation and atomic identification described as the first object, the electron detection instrument having a signal reception section in which a signal detection area detecting signals caused by electrons from a specimen with high sensitivity and resolution thereby can be set arbitrarily was used in combination with the electron detection instrument controller controlling the electron detection instrument to set the signal detection area in the signal reception section. The electron detection instrument above mentioned, usually comprises a scintillator and an imaging device. In this case, the imaging device which can set a photodetection area (as a signal detection area) arbitrarily on a photon reception section (as a signal reception section) was employed.

The imaging device used is an avalanche-type imaging device having amorphous-selenium photoconductive-film thereof or a CCD (charge-coupled device). A contour of the photodetection area of the avalanche-type imaging device is set by controlling an electron beam deflecting system to control a contour of scanning the electron beam emitted from an electron gun for signal detection that is equipped in the imaging device. A contour of photodetection area of the CCD is set by selecting activated one of a multiple of pixels arrayed. Each of the contours of photodetection areas of the imaging devices is controlled by a computer to change depending on an angle distribution of intensities of the electrons to be detected.

The scintillator for the avalanche-type imaging device consists of metal oxo silicate doped with cerium with 350 to 450 nm peak luminescence wavelength. A transparent substrate of the imaging device is preferable to be structured to have an optical fiber plate and a flatting layer laminated together.

The flatting layer is formed as follows. An optical fiber plate is painted with liquid or powder glass. A Si single crystal wafer and an optical fiber plate are pressed together with the wafer fitted with the glass. In pressing, they are heat-treated. After that, the Si single crystal wafer processed in a back-etching way or the flatting layer is formed by thin glass plate stuck with the optical fiber plate by a bond.

Therefore, the electron detection instrument of the present invention can set the photodetection area of the imaging device as needed so that a detection angle range of the electron beam emitted from the specimen can be set as desired. Therefore, intensities of the scattered, diffracted, refracted, or transmitted electrons through the specimen can be detected in the desired angle range depending on the angle distribution of the electrons. The emission angle distribution of the intensities of the scattered electrons depends on an atomic number of an atom of the specimen. The angle range of detection thus should be set at an angle position at which the scattered electron intensity from the atom is maximum. This makes it possible to enhance the image contrast of the definite atom on the electron microscope image. In particular, if the intensities are detected at a high angle, atomic species determination can be made by quantitatively analyzing the contrasts. The intensity distribution of the diffracted electrons contains information of array of the atoms. This makes it possible to analyze the orientations of the crystal faces, arrays of impure atoms, and shapes and distribution of crystal defects from the position of diffraction spots and the broad pattern.

The detection angle range of the electrons can be set as desired as described above. The detection angle range can be divided into, for example, a central and peripheral areas, from which signals are detected. The central and peripheral areas make it possible to detect the respective transmitted electrons and high-angle scattered electrons simultaneously. As the imaging device has the pixels arrayed in two dimensions, it is possible to measure not only the intensities of the electrons, but also distributions, for example, diffraction pattern and images. Consequently, only one unit of the electron detection instrument of the present invention can measure the high-angle scattered electrons for 3-dimensional atomic arrangement observation and atomic identification, transmitted electrons for conventional electron microscope image, and diffracted electrons for electron diffraction pattern.

The electron detection instruments of the present invention can also measure a weak electron beam at a high accuracy and high signal-to-noise ratio with use of the avalanche-type imaging device having an amorphous-selenium photoconductive-film thereof as the imaging device and with use of the metal oxo silicate doped with cerium as the electron-photon converting scintillator without the photomultiplier and image intensifier to intensify the beam. The reason is explained below.

FIG. 7 depicts a table illustrating characteristic comparisons of the photomultiplier, the prior photomultiplier type imaging device, and the avalanche-type imaging device having an amorphous-selenium photoconductive-film thereof. It is defined here that primary quantum efficiency is number of photoelectrons produced when one photon comes in the photoconductive-film. It is also defined that multiplication factor is a ratio of current output of the imaging device to current of the photoelectrons. The primary quantum efficiency is determined by material of the photoconductive-film. The photoconductive-film of the photomultiplier is formed of $Na_2KSb-Cs$, that of the prior photoconduction-type imaging device of $Sb_2S_3$, ZnCdTe, or the like, and that of the avalanche-type imaging device of amorphous Se. We can see from the figure that the amorphous Se has the highest efficiency in converting the photon to photoelectron. The multiplication factor of photomultiplier is ordinarily around $10^5$ times since the electrons produced in the photoconductive-film are multiplied by a multiple of diode stages. The prior photoconduction-type imaging device cannot multiply the electrons since its photoconductive-film is formed of $Sb_2S_3$, ZnCdTe, or the like. The avalanche-type imaging device does avalanche multiplication of the electrons in the photoconductive-film by applying a high electric field of around $10^6$ V/cm to the photoconductive-film. The multiplication factor achieved is 1,000 times at maximum, depending on the electric field applied to the photoconductive-film (FIG. 8). The sensitivity is a product of the primary quantum efficiency by the multiplication factor. The photomultiplier therefore has the highest sensitivity, but is low in the signal-to-noise ratio that determines the image quality. The reason is that the primary quantum efficiency is low and high noises are produced when little photoelectrons are forcibly photomultiplied by the diodes. The prior photoconduction-type imaging device has not a high primary quantum efficiency, but is high in the signal-to-noise ratio since the multiplication factor is 1. As the sensitivity is low, however, the image intensifier is inevitable together to detect weak electron beam that forms the electron microscope image. If the image intensifier magnifies the electrons 100 times, for example, extensive quantum noises appear, resulting in extreme deterioration of the signal-to-noise ratio. On the other hand, the avalanche-type imaging device having an amorphous-selenium photoconductive-film thereof provides high sensitivity and signal-to-noise ratio enough to measure the electron microscope image. The reason for the high signal-to-noise ratio is that the primary quantum efficiency is high and excessive noises are quite low as well. The excessive noises depend on a ratio of the electrons produced in the photoconductive-film to an ionization constant of the holes. As the ratio is high, the excessive noises are high. The amorphous selenium is featured in that the ratio is lower than the other materials with a high electric field applied.

FIG. 9 depicts a graph illustrating the relative sensitivity of the avalanche-type imaging device having an amorphous-selenium photoconductive-film thereof. We can see from the figure that the relative sensitivity is highest at light wavelength of 400 nm. The light wavelength for maximum emission therefore is 420 to 430 nm with use of the metal oxo silicate (chemical formula: $RE_2SiO_5$) doped with cerium as the electron-photon converting scintillator, particularly with RE being Gd, Y, or Lu. By using the scintillators, the primary quantum efficiency of the image device becomes higher than 98%. The sensitivity of the imaging device of the electron noise can be obtained to the maximum limit.

The optical lenses in the optical system of electron detection instrument can be eliminated by the way that the transparent substrate of the imaging device is structured to have the optical fiber plate and the flatting layer laminated together. This can reduce so high a light intensity loss due to the optical lenses that the detection sensitivity of the electron beam can be increased as much as about five times. The flatting layer also provides the following advantage. The optical fiber plate has minute irregularities of around $0.2\,\mu m$ remained on the surface only after the plate is optically polished. The avalanche-type imaging device having the sensitivity leaped greatly high that is a high sensitivity image tube, has the electric field concentrated at the irregularity because of high operation electric field. The concentration destructs the dark current preventive function locally. As a result, it is a problem that the local dark current is increased, which causes white scratches on the image. The above-mentioned flatting layer can reduce the concentration of the electric field to the irregularities on the surface to a great extent since the irregularities is less than 10 nm, thus thereby successfully solving the above-mentioned problem.

A scattering angle limiting aperture for selecting the scattering angle range from the inside to the outside of scattered electrons used for imaging is installed between a specimen and the electron detector. The scattering angle limiting aperture is a thin plate having a plurality of circular or doughnut-shaped openings and each opening has a different opening diameter. When a scanning transmission electron microscope has a plurality of imaging lenses, a scattering angle limiting aperture is installed between some lenses adjacent to the imaging lenses. In the electron detection system, only one electron detector having a circular scintillator for converting electron to photon on the electron detection face is installed.

Electron microscope images used for 3-dimensional reconstruction have an almost linear relation between image contrast and specimen thickness and electrons scattered at a high angle (50 mrad or more) at which the image contrast depends on the atomic number are used for imaging.

BRIEF DESCRIPTION OF THE DRAWINGS

FIG. 1 is an explanatory view showing the principle of image formation using an electron beam with a diameter equal to or smaller than the size of one to two electrons.

FIG. 11 is waveform graphs illustrating control signals in directions X and Y with an electron beam annularly scanned;

FIG. 12 is waveform graphs illustrating another example of control method for the same scanning pattern as in FIG. 7;

DETAILED DESCRIPTION OF THE PREFERRED EMBODIMENTS

Referring to the diagrams described briefly above, embodiments according to the present invention are explained as follows.

[EMBODIMENT 1]

Figure 5:
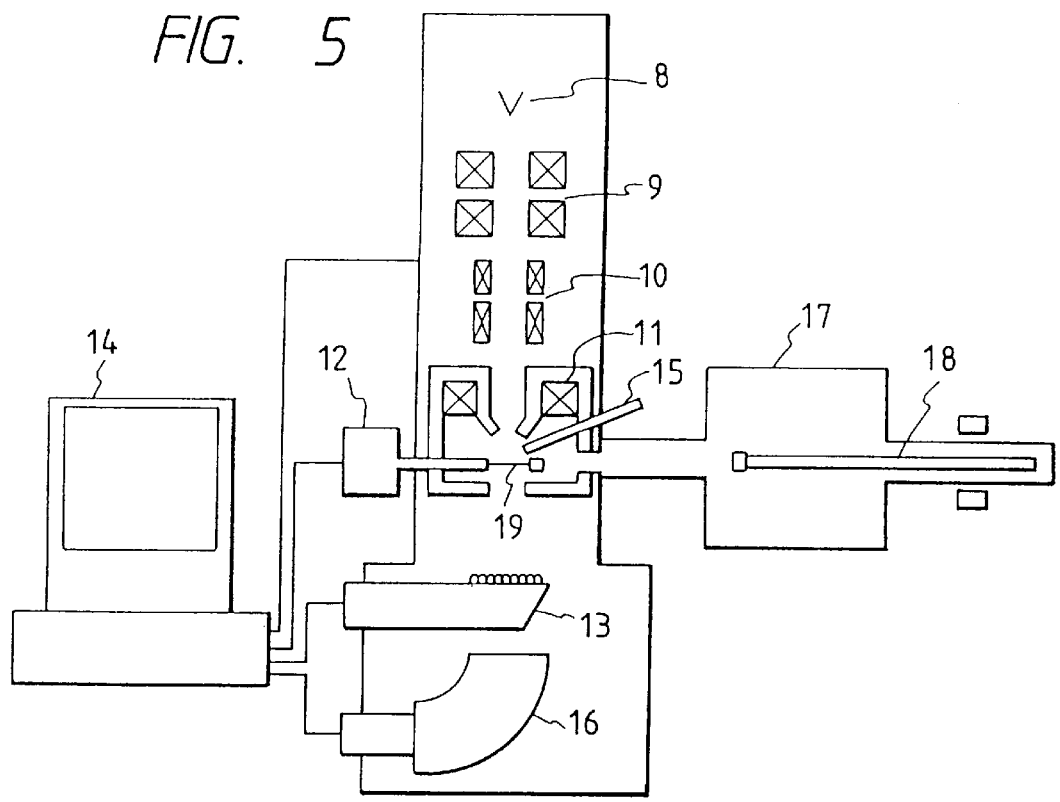
FIG. 5 is a diagram showing an overall structure of the embodiment 1 according to the present invention.

FIG. 5 is a diagram showing a basic configuration of an electron-microscope apparatus used in the embodiments according to the present invention. As shown in the figure, the apparatus comprises a field emission electron gun 8, condenser lenses 9, electron deflector coils 10, object lenses 11, a specimen goniometer/tilting system 12, an electron detector 13, a computer 14 for executing control and image-processing software, an X-ray detector 15, an energy analyzer 16, a specimen preparation room 17 and a specimen transfer system 18. In order to generate an electron beam with a diameter equal to or smaller than the size of one to two atoms, an acceleration voltage of at least 200 kV is applied to the field emission electron gun 8 and electrostatic lenses and magnetic lenses (as 9–11) for illumination with small aberration are employed. A specimen 19 is scanned by the beam deflecting/scanning coil 7 by applying an electron beam to the specimen 19. The electron detector 13 has a multi-channel typed matrix of a plurality of photosensitive devices. The intensities of electrons scattered and transmitted by the specimen 19 can be measured by identifying relations between the addresses of the photosensitive devices in the matrix and the scattering angles and directions of the electrons. Even though CCD photosensitive devices are typically employed in the electron detector 13, photosensitive devices of other types with high sensitivity can also be used as well. The specimen goniometer/tilting system 12 comprises a step motor and a goniometer which are controlled by the computer 14. This allows the inclination of the specimen 19 to be adjusted in the milliradian order. So, the positional aberration is compensated in the nanometer order. The computer 14 executes the control and image-processing software, allowing intensities and distribution of electrons measured by the electron detector 13 to be input and stored into memory in synchronization with the scanning operation of the incident electron beam. In addition, the computer 14 is also capable of carrying out a variety of image processings.

Figure 1A:
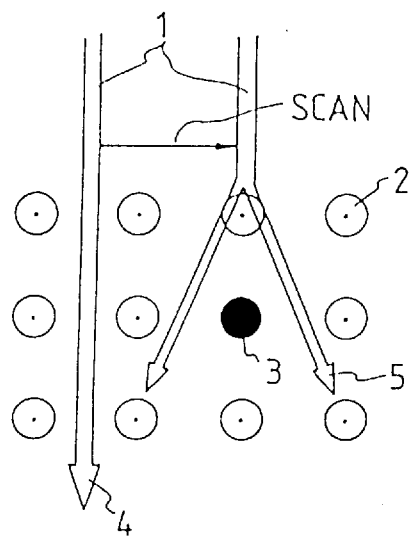
FIG. 1(a) shows states of transmission and scattering electron beams and an electron-microscope image when electron beam is parallel to the direction of atomic columns.
Figure 1B:
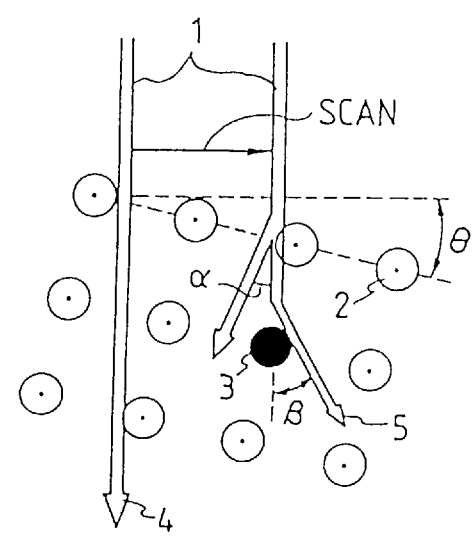
FIG. 1(b) shows states of transmission and scattering electron beams and an electron-microscope image when electron beam has an incident angle θ to the direction of the atomic columns.
Figure 1C:
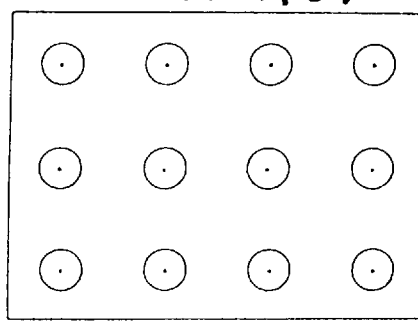
FIG. 1(c) is a projection image of the scan shown in FIG. 1(a).
Figure 1D:
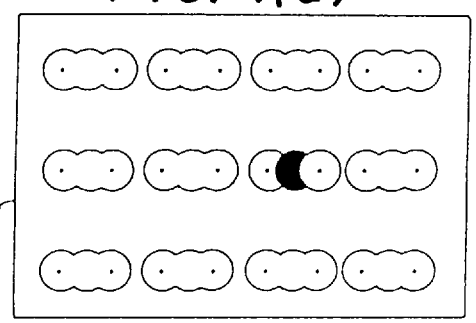
FIG. 1(d) is a projection image of the scan shown in FIG. 1(b) viewed from an inclined direction forming the angle θ with the atomic columns.
Figure 2:
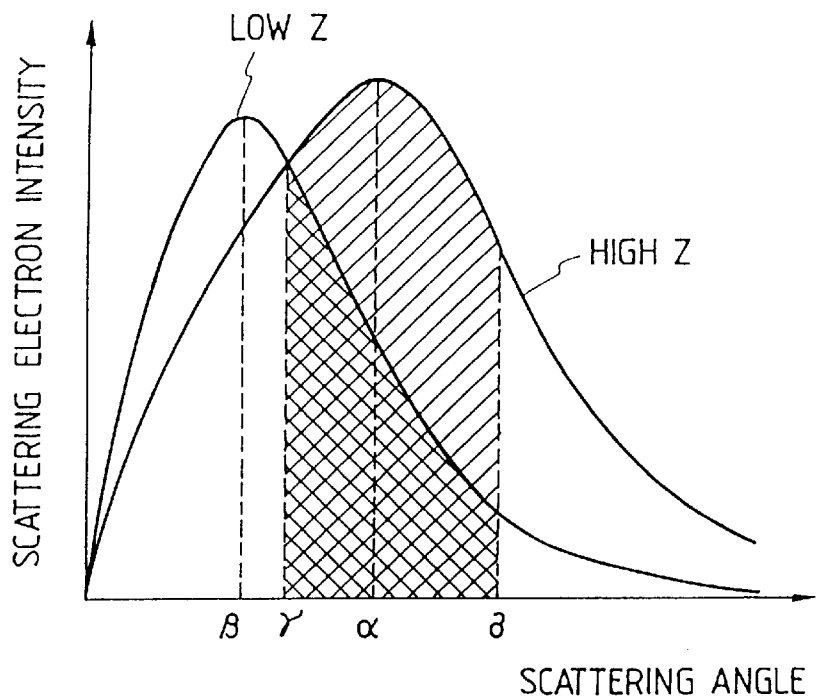
FIG. 2 is an explanatory view showing relations between the scattering electron intensity and the scattering angle for atoms with low and high atomic numbers.
Figure 3:
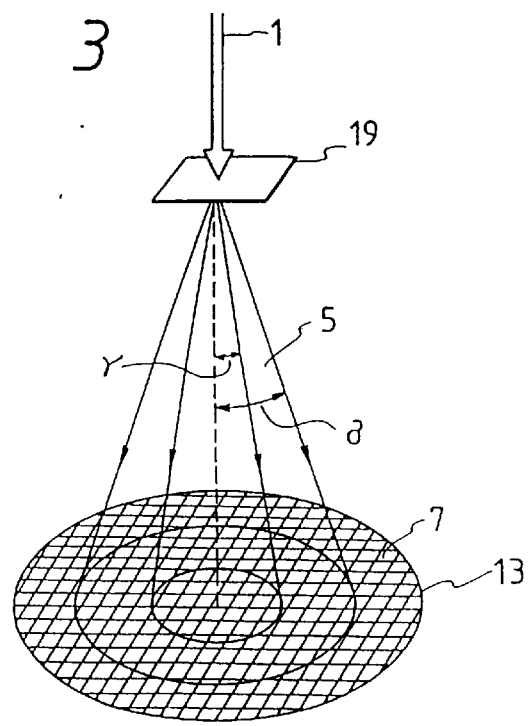
FIG. 3 is an explanatory view for measurement of scattering electrons by a multi-channel electron detector in a scattering angle between γ and δ.
Figure 6:
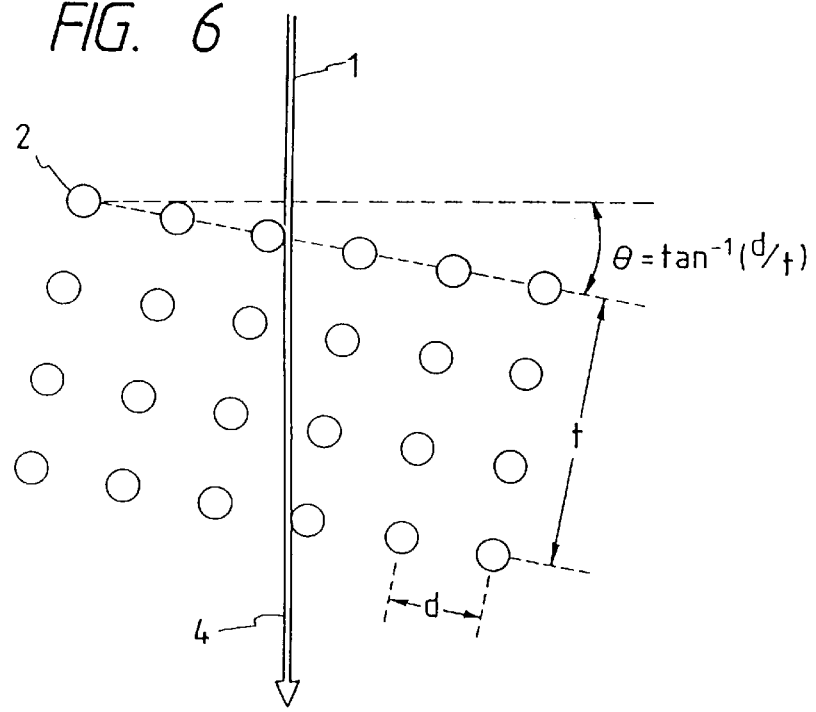
FIG. 6 is an explanatory diagram showing a relation between the angular increment (θ) of the specimen, the distance from an atom to an adjacent one (d) and the thickness of the specimen (t)
Figures 7, 9:
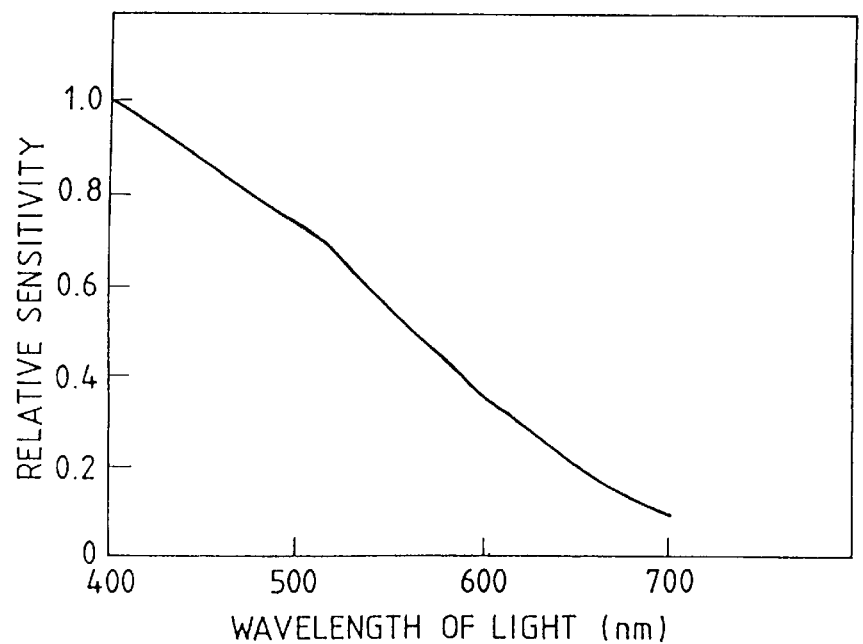
FIG. 7 is a table illustrating characteristic comparisons of a photomultiplier, a prior photoconduction-type imaging device, and an avalanche type imaging device having amorphous-selenium photoconductive-film thereof.
FIG. 9 is a graph illustrating a relative sensitivity of the avalanche-type imaging device having amorphous-selenium photoconductive-film thereof.
Figure 8:
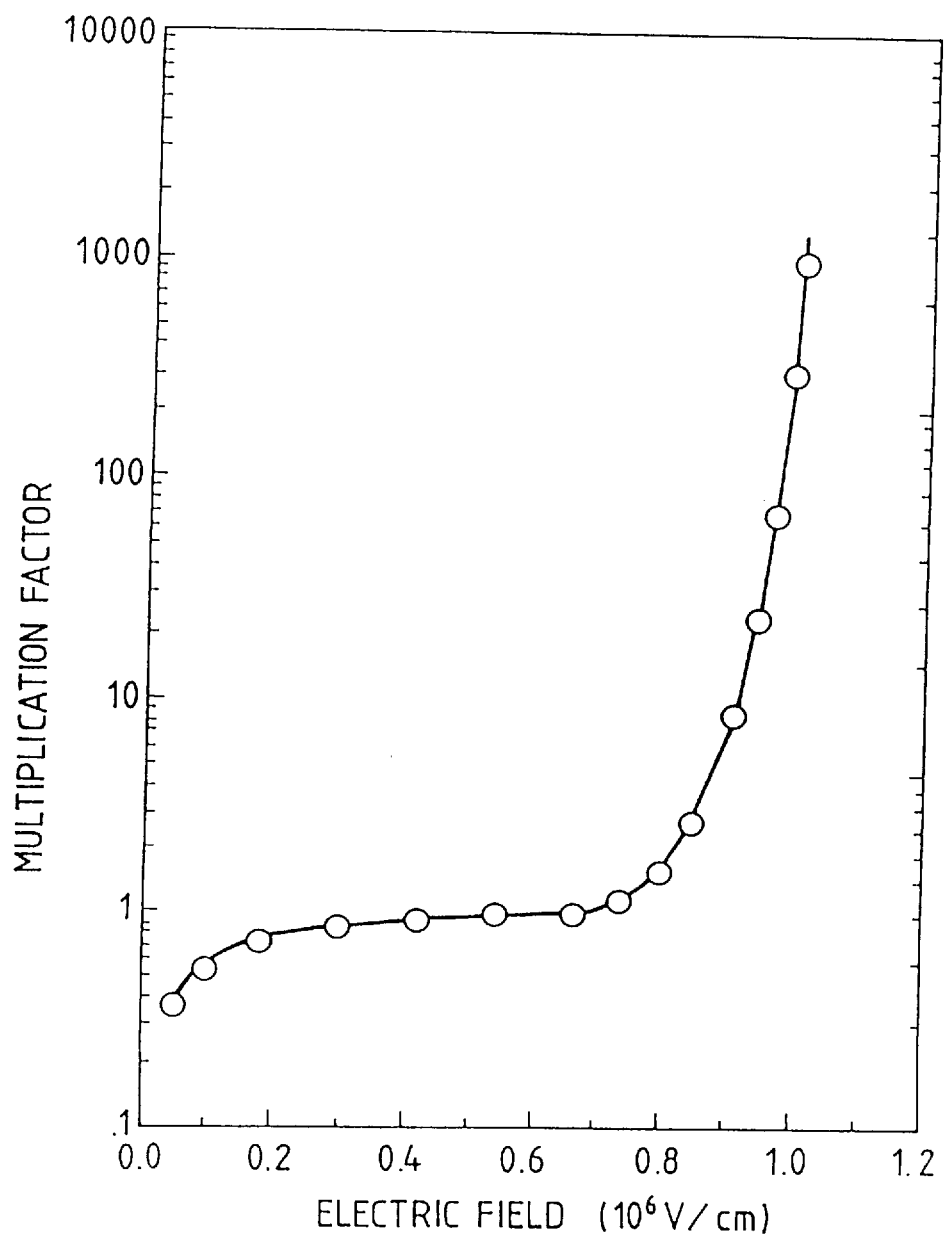
FIG. 8 is a graph illustrating a multiplication factor to an electric field of the avalanche-type imaging device.

Next, a step of observing a 3-dimensional atomic arrangement according to the present invention is described. FIG. 1 shows interaction between an atom 2 constituting the thin-film specimen 19 and incident an electron beam 1 having a diameter equal to or smaller than the size of one to two atoms. FIG. 1(a) shows a case in which the incident electron beam 1 is parallel to the direction of the atomic columns of the thin-film specimen 19. In this case, an electron incident beam 1 between two adjacent atomic columns is transmitted through by a channelling phenomenon without being scattered by the atoms 2. Note that the channelling phenomenon is a phenomenon in which an electron beam 1 is passed through. An incident electron beam 1 hitting an atomic column is scattered by the first atom 2 on the atomic column. By measuring the intensity of a transmitted or scattered electron 4 or 5 in synchronization with the scanning operation of the incident electron beam 1 by means of the electron detector 13, a projection image of atomic arrangement 6 can thus be observed. Next, the thin-film specimen 19 is inclined to form an angle θ with the incident electron beams 1. As shown in FIG. 6, the angle θ is set to a value smaller than $\tan^{-1}$ (d/t), where d is the distance from an atom to an adjacent one on the thin-film specimen 19 and t is the thickness of the thin-film specimen 19. Though the gap between two adjacent atomic columns as seen from the incident direction of the electron beams 1 becomes smaller, a channelling electron exists. As shown in FIG. 1(b), the projection image of the arrangement 6 corresponds to a projection image viewed from an inclined direction forming the angle θ with the atomic columns. In this case, the view of an impure atom 3 is different from that of FIG. 1(a). That is to say, the impure atom 3 in FIG. 1(a) is not visible because it is shadowed by an atom 2 located right above it. In the case shown in FIG. 1(b), however, the different atom 3 is visible. Accordingly, the incident electron beam 1 is scattered also by the impure atom 3. In general, relations between the scattering angle and the intensity of a scattered electron are shown in FIG. 2. As shown in the figure, the scattered electron intensity is distributed among the scattering angles with a peak located at certain scattering-angle values. The distribution curves are flatter for high scattering-angle values. The distribution curves are also different from each other depending upon the atomic number (Z). The larger the value of the atomic number (Z), the more the distribution curve is shifted to the side of large scattering-angle values. Accordingly, a scattering angle β for the peak intensity of electrons 5 scattered by the impure atom 3 is different from a scattering angle α for the peak intensity of electrons scattered by a surrounding atom 2. In this case, the atom 2 has a greater atomic number than the impure atom 3. Taking the distribution shown in FIG. 2 into consideration, the detection angle range of the scattered electrons 5 used in the imaging by the electron detector 13 is set between angles γ and δ shown in the figure. FIG. 3 shows a state of operation of the electron detector 13 for the detection angle range between γ and δ. As shown in the figure, the electron detector 13 has a multi-channel matrix configuration which comprises a plurality of photosensitive devices 7.

When the incident electron beam 1 hits the specimen 19, electrons 5 are scattered at a variety of scattering angles, arriving at the electron detector 13. Only electrons with scattering angles between γ and δ are used for creating a projection image of atomic arrangement 6. That is to say, only the intensities of scattered electrons 5, which are detected by photosensitive devices 7 located between two concentric circles corresponding to the scattering angles γ and δ, are measured in synchronization with the scanning operation of the incident electron beam 1. The range of detection angles is set by specifying the addresses of the photosensitive devices 7 with the computer 14. With such measurement, the difference in contrast between atoms on the projection image can be recognized. In this case, the atom 2 is bright whereas the different atom 3 is dark. By embracing the same principle, the difference can still be recognized even if a vacancy exists at the position of the impure atom 3. Information on distribution of scattered electron intensities for various atoms are stored in the computer 14. Accordingly, the detection angle ranges for the various atoms can be set in the electron detector 13. The various atoms can thus be distinguished from each other based on differences in image contrast between them. In addition, since the specimen goniometer/tilting system 12 allows the inclination angle of the specimen 19 to be controlled in the milliradian order, an inclination angle can be set at the condition of the channelling-phenomenon. Moreover, the position of the specimen 19 can be controlled using the computer 14 so that the target of observation on the specimen 19 is always located at the center of the observation area. The computer-based control is carried out by finding the amount of aberration in the position of the specimen 19, that results with the specimen 19 inclined, using the image processing. By continuously observing images while varying the inclination angle and storing image data in the computer 14, the projection images of atomic arrangement 6 observed from a variety of directions can be obtained.

Figure 4:
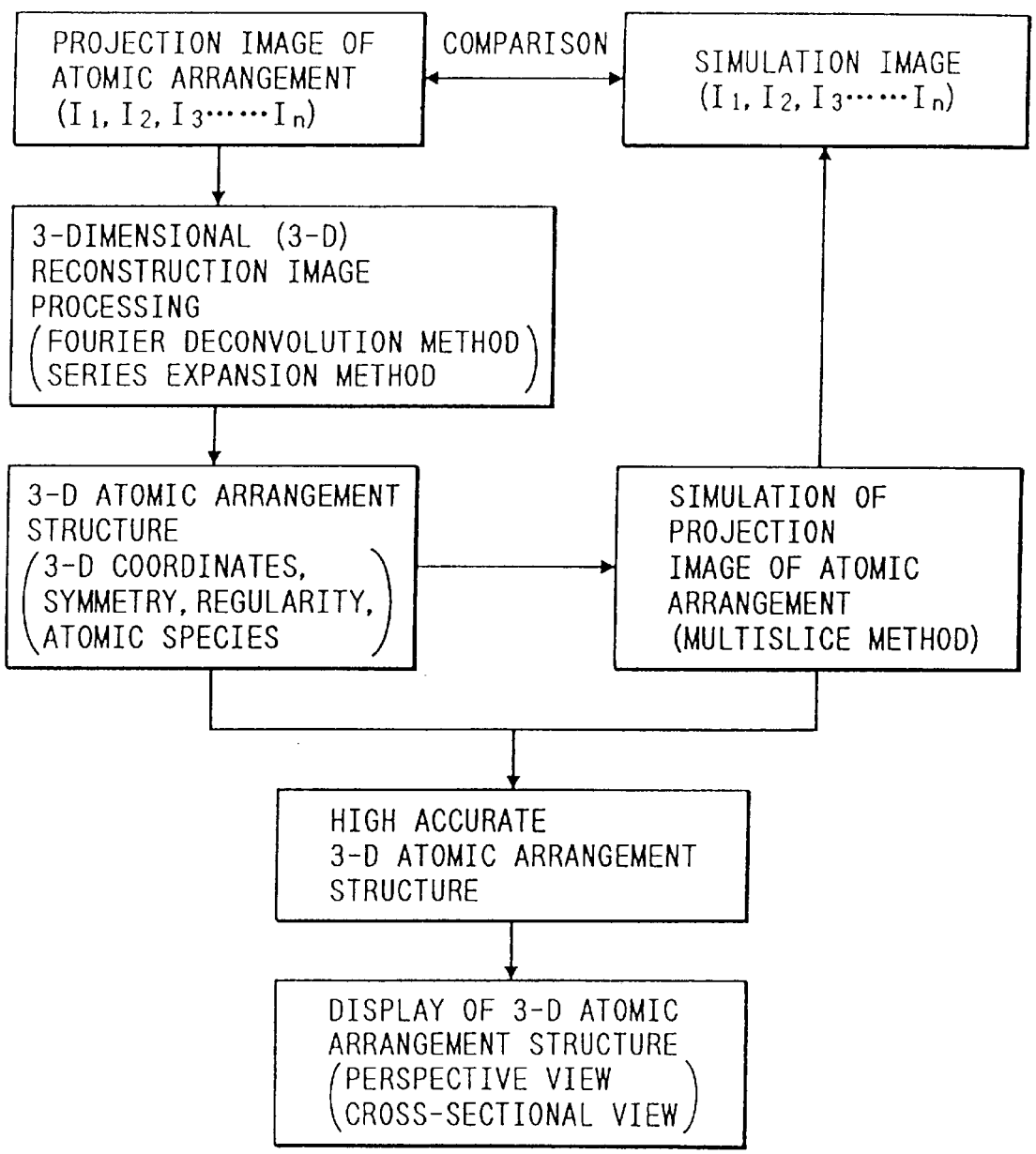
FIG. 4 is an explanatory view showing a process of constructing a 3-dimensional atomic structure by image processing of 2-dimensional atomic images observed at a variety of inclination angles θn of a specimen.

The image processing constructs a 3-dimensional structure of the atomic arrangement based on projection images of atomic arrangement 6 ($I_1$, $I_2$ to $I_n$) obtained at inclination angles ($\theta_1$, $\theta_2$ to $\theta_n$) respectively with a procedure shown in FIG. 4. The 3-dimensional structure of the atomic arrangement is displayed on a CRT of the computer 14. On the procedure, at first, 3-dimensional image processing is performed on the projection images of atomic arrangement 6 ($I_1$, $I_2$ to $I_n$) to identify 3-dimensional coordinates, the symmetry, and the regularity of the atoms. The atomic arrangement identified above are then combined with measurement data of atomic species to determine a 3-dimensional structure of the atomic arrangement of the specimen 19. The technique adopted for constructing the 3-dimensional structure is the same as that described on Page 15 of No. 6, Vol. 17, 1978 of Measurement and Control, a technical journal. The image processing software for constructing the 3-dimensional structure, which is capable of creating a 3-dimensional configuration based upon information obtained even from a range of possible inclination angles 0 to about 20 degrees of a specimen. For example, the softwares are Fourier deconvolution method and the series expansion method. The image processing software is executed by the computer 14 which selects one of the techniques in accordance with the amount of information to be processed. Based on data of the 3-dimensional structure of the atomic arrangement, a projection image of the atomic arrangement 6 is then simulated. Software used in the simulation applies a typical method such as the multi-slice technique. The simulated image is then compared to the observed image in order to confirm whether or not a projection image of the atomic arrangement 6 can be reproduced from the constructed 3-dimensional structure of the atomic arrangement. If the reproduction is impossible, the data of the 3-dimensional structure of the atomic arrangement is corrected to give another simulated projection image of the atomic arrangement 6. This operation is repeated until the simulated image matches the observed one. In this way, the accuracy of the 3-dimensional structure of the atomic arrangement can be enhanced. The 3-dimensional structure of the atomic arrangement determined as such is finally displayed on the CRT of the computer 14 as a squint image or a cross-sectional view seen from any desired direction.

The composition and bonding state of elements constituting the specimen 19 can be analyzed by measurement of a characteristic X-ray by the X-ray detector 15 and measurement of loss energy of transmitted electrons by the energy analyzer 16. A scanning tunnelling microscope is installed at the specimen preparation room 17 in which the thinning process of the specimen 19 is carried out by utilizing a field-evaporation effect that occurs when a field is applied to an area between a tip and the specimen 19. In this way, atoms are stripped off one by one. Accordingly, the thickness of the specimen 19 can be controlled in atomic-layer order without damaging the specimen 19 at all. By carrying out the operation to strip off atoms as such while observing the specimen 19 through the scanning tunnelling microscope, the structure of an infinitesimal portion of interest can be surely converted into a thin film with an accuracy at the atomic level. Since the thin-film specimen 19 is conveyed by the specimen transfer system 18 to a specimen observation room through a vacuum, the specimen 19 is neither contaminated nor oxidized. In the specimen preparation room 17, the specimen 19 can undergo manufacturing and fabrication processes such as the specimen cleaning and alteration using ion radiation and heating and the thin-film formation using evaporation and sputtering. Therefore, atomic structures in a variety of states can be observed. Furthermore, the specimen preparation room 17 can be removed from the electron microscope and connected to the actual thin-film equipment used in the semiconductor process. In such an arrangement, a specimen formed by the thin-film equipment is conveyed to the apparatus provided by the present invention in which the evaluation of its process conditions can be carried out.

As described above, the present invention allows the observation of the 3-dimensional atomic arrangement at a high resolution of higher than 0.2 nm. The present invention also allows the analysis of atomic species. In addition, the present invention allows the composition and the bonding state to be measured as well. Point defects, impure atoms and their clusters which are difficult to examine using the conventional electron microscope can thereby be observed at a single-atomic level. Accordingly, the causes of ULSI devices' defects, thin film's formation conditions and the like can be evaluated at high accuracy. In the case of the conventional electron-microscope techniques, as many specimen samples as numerous observation directions have to be prepared in order to accomplish 3-dimensional observation. With the present invention, however, only a single specimen is required. As a result, the T. A. T. (turn-around time) of the evaluation process is substantially reduced as compared to that of the conventional techniques.

[EMBODIMENT 2]

Figure 10:
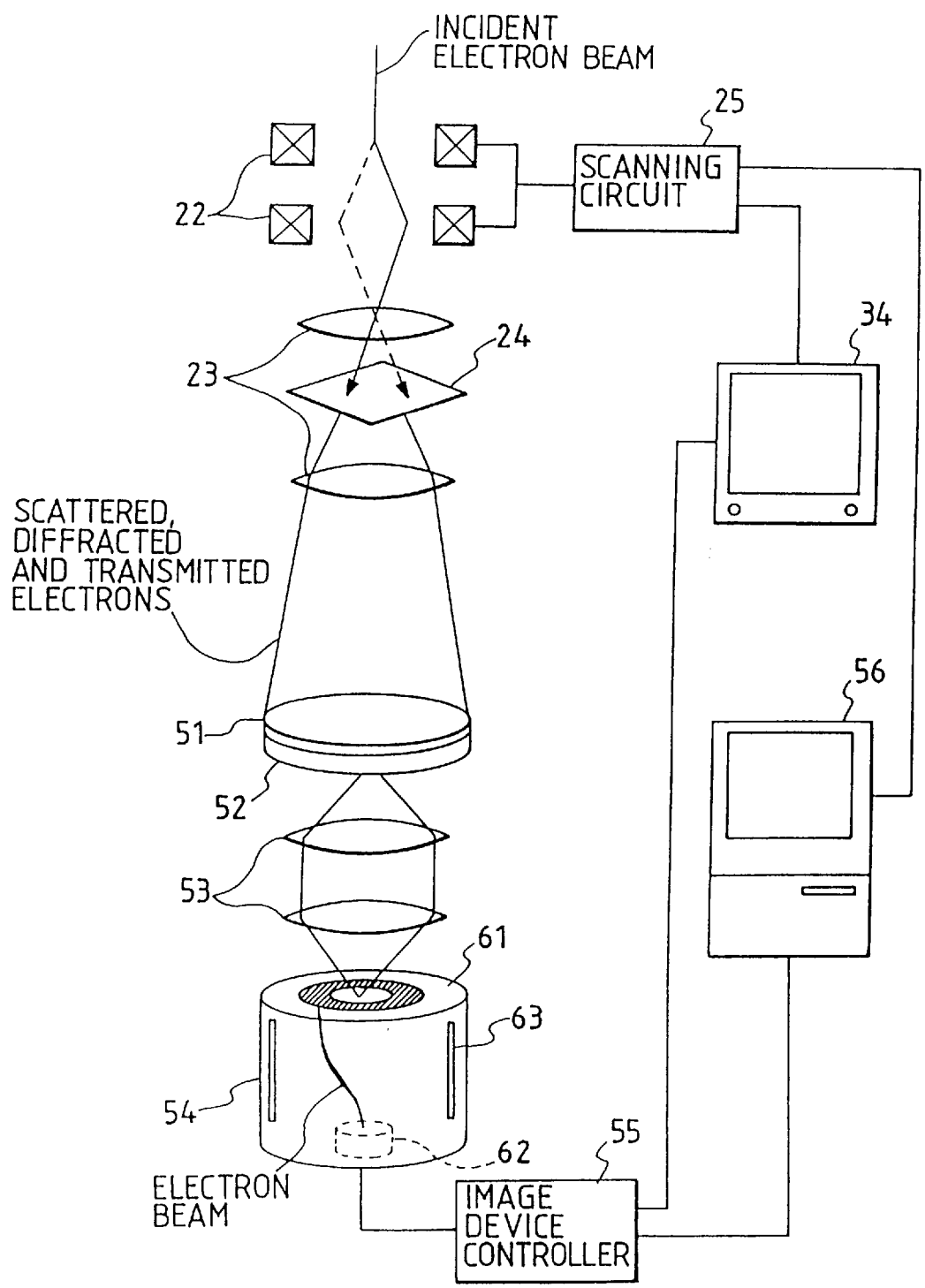
FIG. 10 is an exploded perspective view and a block diagram illustrating an overall configuration of an electron detection instrument for electron microscope used in a first embodiment according to the present invention.

FIG. 10 depicts an exploded perspective view and a block diagram illustrating a basic configuration of an electron detection instrument for electron microscope used in this embodiment according to the present invention. The electron microscope used in this embodiment (overall structure is not shown in FIG. 10) has almost same structure as the embodiment 1 except for the electron detection instrument. The electron detection instrument comprises a scintillator 51, a substrate (e.g. a transparent substrate) 52, optical lenses 53, an avalanche-type imaging device 54 having a photoconductive-film of amorphous selenium, an imaging device control system 55, a computer 56, and a monitor 34. The computer 56 and the monitor 34 are connected with a scanning circuit 25 for energizing deflection coils 22 that scan an incident electron beam of the electron microscope on a specimen 24. The computer 56 and the monitor 34 can have a scanning signal input from the scanning circuit 25. The computer 56 can also synchronize the imaging device 54 through its control system 55 with the scanning circuit 25.

The scintillator 51 is a converter for converting to light intensity distribution an intensity distribution of scattered, diffracted, refracted, or transmitted electrons through the specimen. In this embodiment, the avalanche-type imaging device 54 having the photoconductive-film of amorphous selenium is used. Accordingly, a scintillator 51 material used is a metal oxo silicate doped with cerium that has a luminescence wavelength at which the imaging device has a highest primary quantum efficiency. Conditions for the scintillator 51 include high photon emission, little deterioration, and narrow expansion of incident electron beam accelerated by 100 to 300 keV. The above-mentioned scintillator 51 meets those conditions. The crystal may be either of polycrystal or single crystal. The scintillator 51 should be made several ten mm in thickness so that the incident electron beam should not become wide not to make fuzzy the electron microscope image. The scintillator 51 should have an Al film of several ten nm evaporated on a surface thereof to prevent charge-up.

The optical lenses 53 are used for focusing on a photon reception surface of the avalanche-type imaging device 54 the electron microscope image converted to photon image by the scintillator 51. The lenses used should be short focal distance and low F value relative to an aperture thereof to make little light intensity loss. The above-mentioned optical lenses 53 should be focused on a bottom of an optical fiber plate if the substrate 52 of made of the optical fiber plate or on a bottom of the scintillator 51 if the substrate 52 of made of glass. The latter can make lower the light intensity loss and increase the sensitivity of the electron detection instrument. The lower lens should be focused on the photoconductive-film 61 of the avalanche-type imaging device 54.

In the avalanche-type imaging device 54 the photons produced by the scintillator 51 emit electron-photon pairs in the photoconductive-film 61 of the photon reception surface thereof (upper surface in FIG. 10). The generated current is detected by an electron beam emitted from an electron gun 61 of the avalanche-type imaging device 54 to obtain an output signal. The photoconductive-film 61 makes an avalanche multiplication of the current produced by the incident photons as a higher electric field than $10^6$ V/cm is applied between its upper surface and lower surface (electric applying means is not shown). The avalanche-type imaging device 54 thus can obtain a gain higher than 60 times the ordinary imaging device. The electron beam is scanned on the lower surface of photoconductive-film 61 at a TV rate of 1/30 sec per screen. The intensity distribution of the photons projected to the photoconductive-film 61 therefore can be picked up in the same way as an ordinary TV camera.

Figure 18:
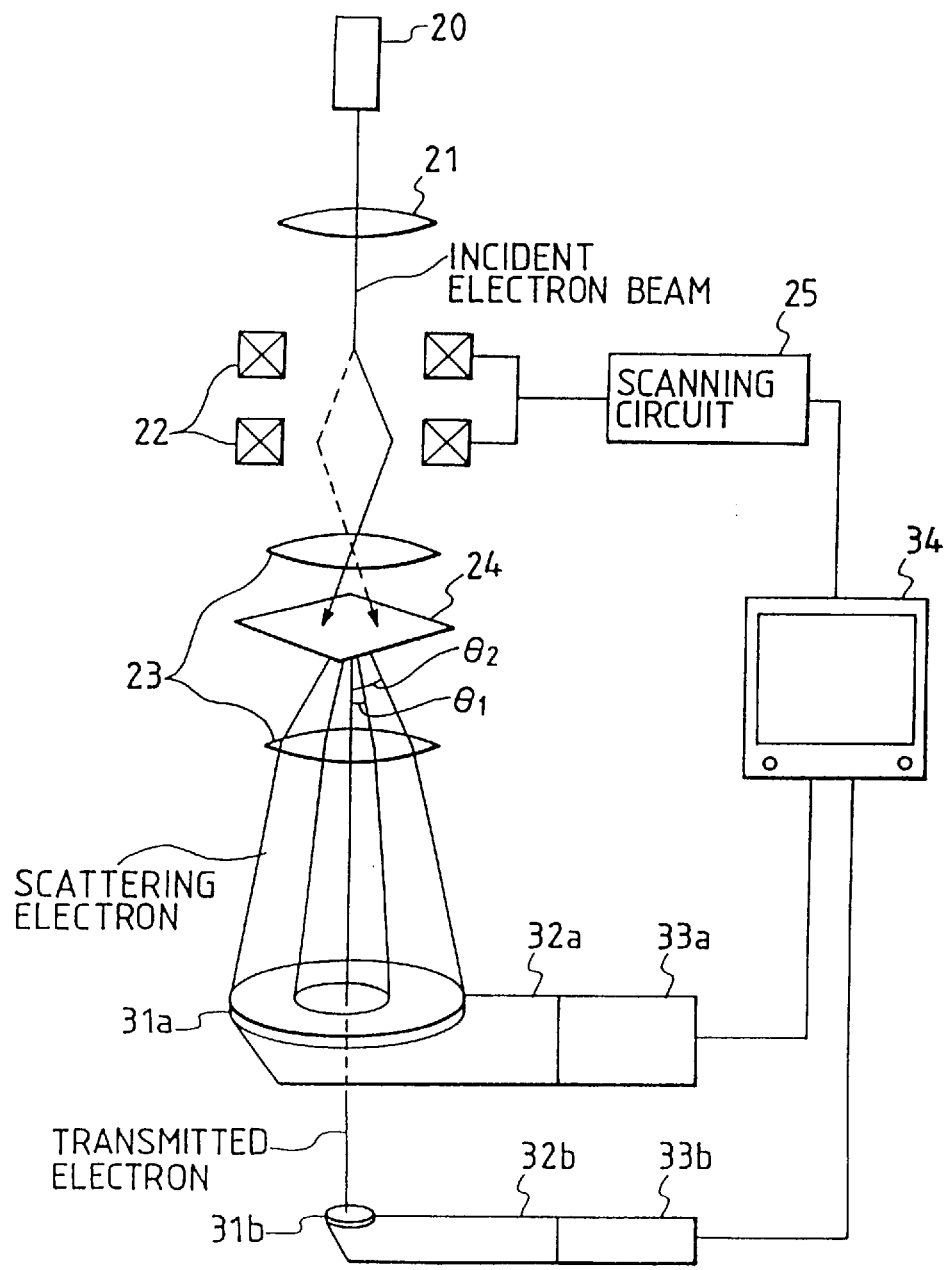
FIG. 18 is an exploded perspective view and a block diagram illustrating an overall configuration of a prior electron detection instrument implemented in an electron microscope.
Figure 19:
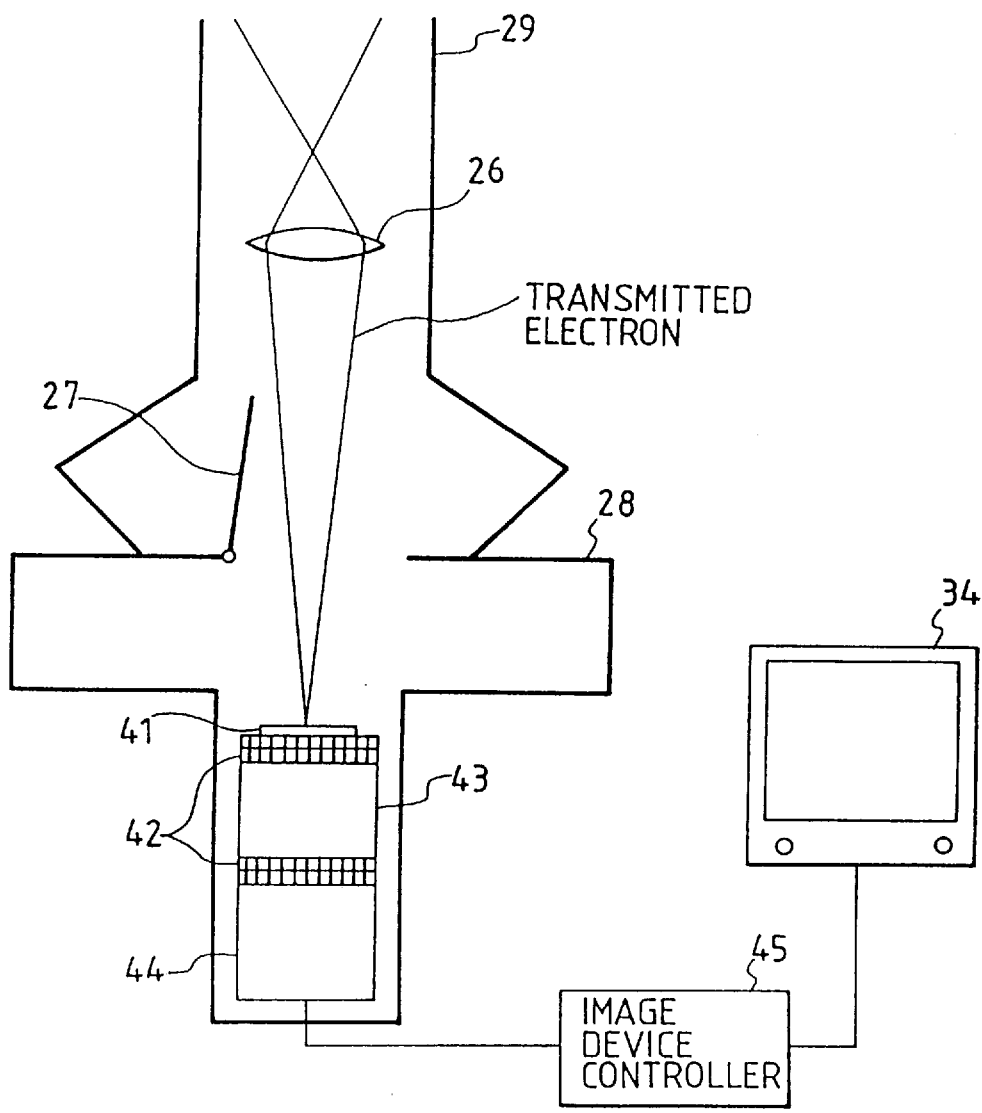
FIG. 19 is an exploded perspective view and a block diagram illustrating an overall configuration of a prior imaging instrument implemented in an electron microscope.

The imaging device control system 55 controls the input and output of the avalanche-type imaging device 54. The imaging device control system 55 controls the deflection electrodes 63 for scanning the electron beam for signal detection to set a contour of detectable area of the whole area of the photoconductive-film 61. If the contour of detectable area is controlled as an annular, the electron detection instrument operates as annular detector for observing a dark-field image only with electrons scattered at the high angle shown in FIG. 18. Similarly, the electron detection instrument also operates as circular detector for observing a bright-field image only with transmitted electrons.

The above-mentioned electron beam for signal detection is controlled as follows. FIG. 11 depicts waveform graphs illustrating control signals in directions X and Y with the electron beam scanned annularly. Symbols a to c indicated above the control signal waveforms correspond to positions a to c of a pattern of the scanned electron beam shown right. FIG. 12 depicts waveform graphs illustrating another example of control method for the same scanning pattern as in FIG. 11. The figure shows only the graphs in the direction X as the control signal waveforms in direction Y are same as in FIG. 11. In the method in FIG. 12, the electron beam emission of the electron gun is controlled at the same time as the scanning control of the electron beam. This can obtain the same scanning pattern as in FIG. 11.

With the avalanche-type imaging device 54, the scanning position of the electron beam for signal detection corresponds to the pixel position. The size of pixel, or resolution, is around 10 mm, depending on diameter of the electron beam for signal detection. Signals output of the imaging device control system 55 can be obtained from the pixels independently. By adding the signals output from the pixels in operation, the intensity of all the detected electron can be measured. If the signals of the pixels are detected in accordance as array of the pixels, they become image information.

The computer 56 controls the imaging device control system 55 and A–D converts and records the electron beam intensity signal and the image signal fed from the imaging device control system 55. The recording is made in correspondence to the scanning position of the incident electron beam on the specimen on the basis of the signal from the scanning circuit 25. The monitor 34 can either display the image signal from the imaging device control system 55 as image directly, for example, an electron diffraction pattern, or display the STEM (scanning transmission electron microscope) image in a way that the electron beam intensity signal is synchronously brightness-modulated with the scanning signal from the scanning circuit 25.

Figure 13:
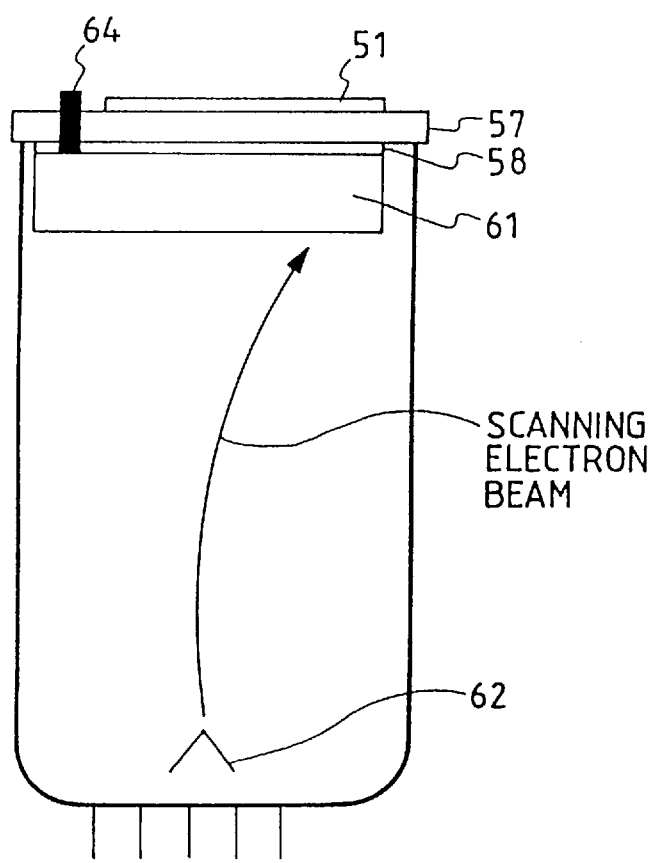
FIG. 13 is an overall elevation view illustrating an example of the avalanche-type imaging device structured as described.

In this embodiment is used the optical lenses 53 in the optical system of the electron detection instrument. To increase the sensitivity further, the transparent substrate of the imaging device should be structured to have the optical fiber plate and the flatting layer laminated together. FIG. 13 depicts an elevation view illustrating an example of the avalanche-type imaging device 54 structured as described above. The example comprises an optical fiber plate 57, a transparent electrode 58, an photoconductive-film 61, a signal pin 64, a cathode 62, and a scintillator 51. The signal light fed out of the scintillator 51 arranged in contact with the optical fiber plate 57 can made to come fully to the photoconductive-film 61 by the optical fiber plate 57 of 100% numerical aperture to generate signal charge. It is desirable to apply so high electric field between the transparent electrode 58 and the cathode 62 through the transparent electrode 58 as to cause avalanche multiplication of charge in the photoconductive film. This can increase the signal charge generated in the photoconductive-film in an avalanche fashion. The signal charge is read by the scanned electron beam. As a result, a super-high sensitivity characteristic is accomplished together with an effect of the optical fiber plate 57 having little light intensity loss.

Figure 14:
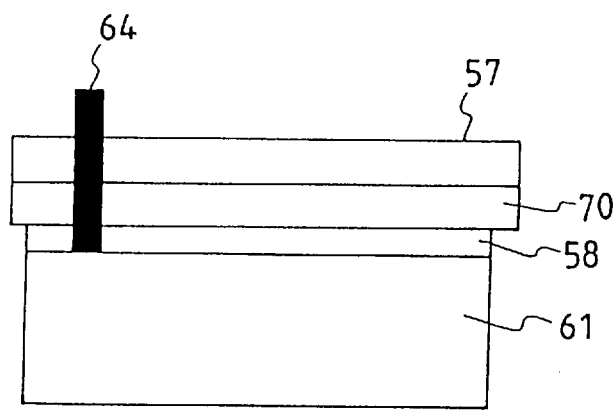
FIG. 14 is an elevation view illustrating an example of eliminating irregularity on a surface of an optical fiber plate according to the present invention.

FIG. 14 depicts an elevation view illustrating an example of eliminating irregularity on the surface of the optical fiber plate 57 by the flatting layer. The example comprises an optical fiber plate 57, a flatting layer 70, a transparent electrode 58, an photoconductive-film 61, and a signal pin 64. The flatting layer 70 should be thinner than at least 10 mm to make it transparent for the visible light and not to cause photon scattering in the flatting layer to deteriorate the resolution. The flatting layer should be prepared in the method given below.

Figure 15:
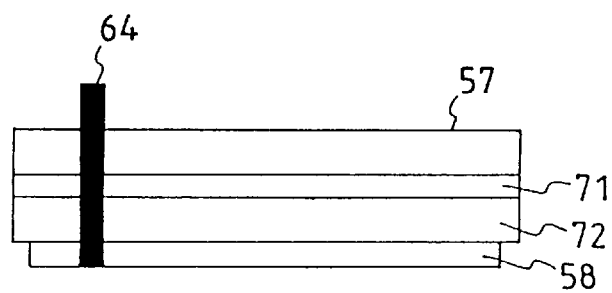
FIG. 15 is an elevation view illustrating an example of process of flatting on the surface of the optical fiber plate.

FIG. 15 depicts an elevation view illustrating an example of process of flatting on the surface of the optical fiber plate 57 according to the present invention. The example comprises the optical fiber plate 57, a bond 71, a thin plate glass 72, the transparent electrode 58, and the signal pin 64. Firstly, the optical fiber plate 57 of one inch diameter should be optically polished in a way similar to ordinary glass polishing. Secondly, the polished optical fiber plate 57 should be bonded with the thin plate glass 72 of 500 μm thick by the bond 71. The bond 71 used was of ultraviolet rays hardening type that has little expansion coefficient when it is solidified. To prevent the bond 71 from absorbing and scattering photons, the bond 71 was made thinner than 1 μm by way of spin painting. After the bond 71 was solidified, the thin plate glass 72 was polished to around 10 μm by way of optical polishing. The thin plate glass 72 was cleaned with an organic solvent. Then, surfaces of the thin plate glass 72 was further dry-etched in an Ar gas atmosphere at 10.6 pascal of partial pressure of Ar to increase the flatness. After that, the thin plate glass 72 was painted with ITO (indium tin oxide) of 0.8 μm thick by sputtering evaporation. The painted thin plate glass 72 was dry-etched in an Ar gas atmosphere like the above again so that the ITO should be around 0.2 μm in the thickness. With the process described above, a surface of the ITO becoming the transparent electrode 58 can be finished to less roughness than 1 nm.

The full process of flatting the optical fiber plate 57 was explained above. If the surface of the thin plate glass 72 is good, sputtering and dry-etching the ITO can be omitted. Just after dry-etching the thin plate glass 72, the ITO may be evaporated onto the transparent electrode 58 to around 100 nm thick. This can complete the flatness.

Figure 16:
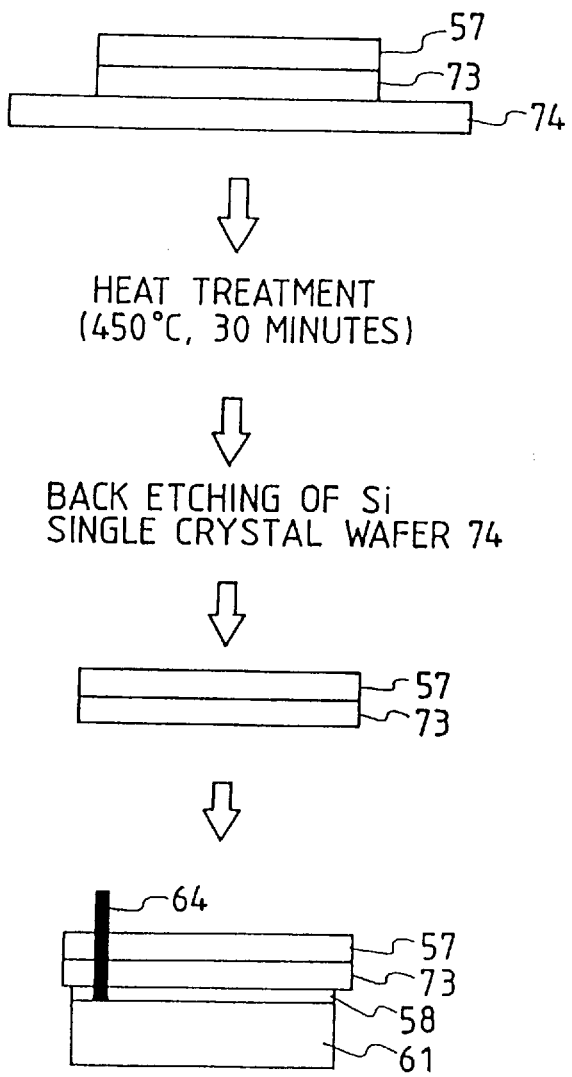
FIG. 16 is flow procedures illustrating another example of process of flatting on the surface of the optical fiber plate.

FIG. 16 depicts flow procedures illustrating another example of process of flatting on the surface of the optical fiber plate 58 according to the present invention. The example comprises the optical fiber plate 57, an SOG (spin on glass) 73, and a Si single crystal wafer 74. In the process, firstly, the optical fiber plate 57 of one inch diameter is spin-painted with the SOG 73 on an upper surface thereof to 2 to 3 μm thick by a spinner. Secondly, the Si single crystal wafer 74 and the optical fiber plate 57 are pressed together, with the mirrored surface of the wafer fitted with the SOG. In pressing, they are heat-treated at 450° for 30 min to solidify the SOG. After that, the Si single crystal wafer 74 is optically polished to around 100 μm thick. In turn, the substrate is immersed in a hydrazine solvent to back-etch the Si single crystal wafer 74. The Si single crystal wafer 74 is completely etched in around two hours. The optical fiber plate 57 has a $SiO_2$ surface formed by the heat treatment of the SOG. The $SiO_2$ surface has excellent flatness since the mirrored surface of the Si single crystal wafer 74 is transferred thereto.

On the surface of SOG 73, the transparent electrode 58 is formed as the process shown above (referring FIG. 15), and furthermore the photoconductive-film 61 is formed on this electrode 58.

The first embodiment uses the inorganic SOG. Alternatively, an organic SOG or powder glass can be used to provide equivalent flatness.

In this embodiment, the present invention provides the electron detection instrument for an electron microscope and its manufacturing method. This electron detection instrument has higher sensitivity than prior instruments, and enable to the rapid detection of a weak electron beam such a high-angle scattered electron beam. Thus the electron microscope shown in this embodiment is suitable for 3-dimensional atomic arrangement observation and atomic identification at higher speed.

[EMBODIMENT 3]

Figure 17:
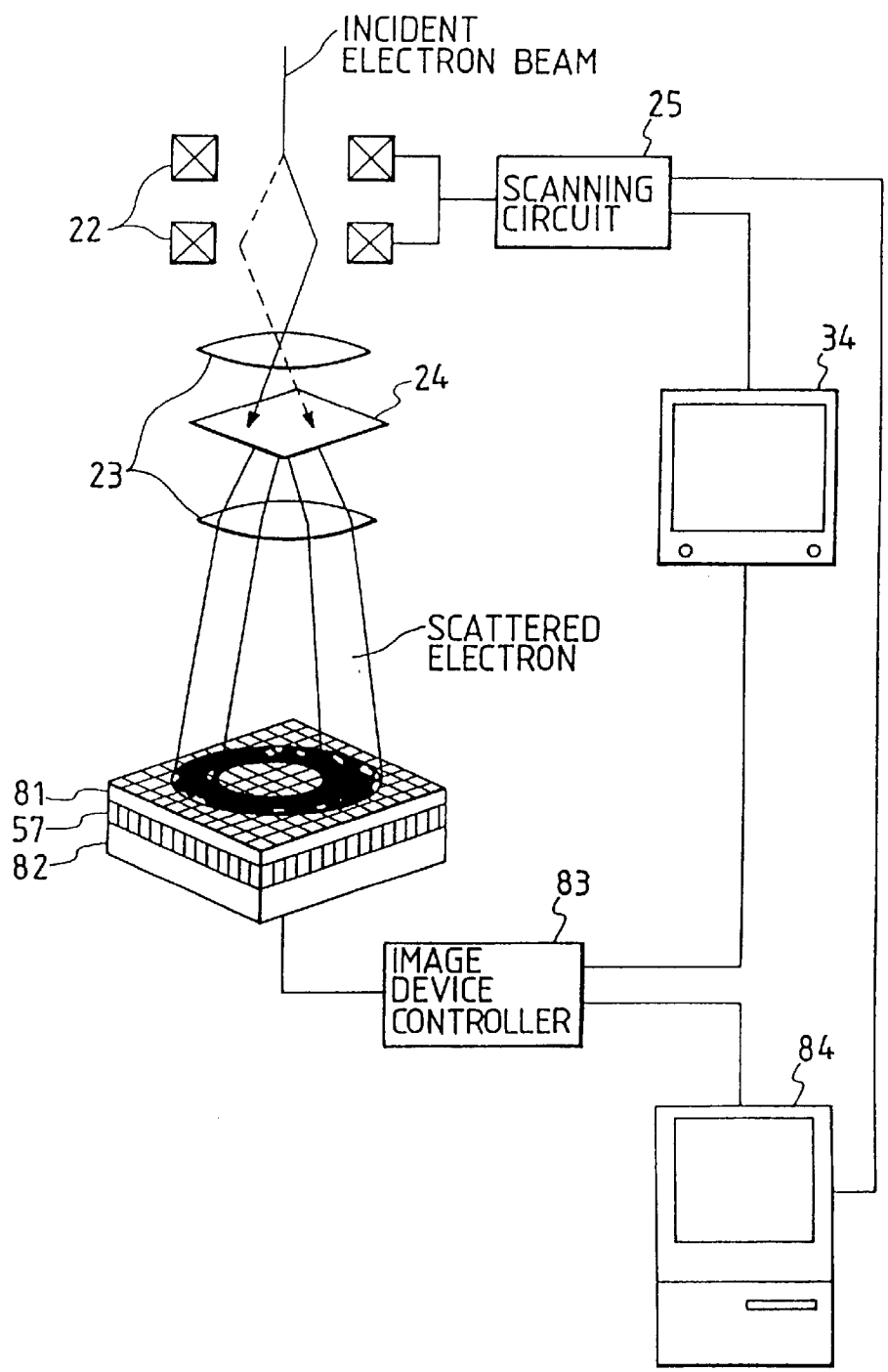
FIG. 17 is an exploded perspective view and a block diagram illustrating an overall configuration of an electron detection instrument for electron microscope used in a second embodiment according to the present invention.

FIG. 17 depicts an exploded perspective view and a block diagram illustrating a basic configuration of an electron detection instrument for electron microscope used in a second embodiment according to the present invention. The electron microscope used in this embodiment (overall structure is not shown in FIG. 17) has almost same structure as the embodiment 1 except for the electron detection instrument. The electron detection instrument comprises a scintillator 81, an optical fiber plate 57, a CCD imaging device 82, an imaging device control system 83, a computer 84, and a monitor 34.

The scintillator 81 has a YAG ($Y_{3-x}Ge_xAl_5O_{12}$) of 550 nm peak luminescence wavelength doped with cerium or GOS ($Gd_2O_2S$) of 510 nm peak luminescence wavelength doped with praseodymium, cerium, or fluorine. The optical fiber plate 57 is used to couple the scintillator 81 with the CCD imaging device 82 optically. The scintillator 81 generates photons isotropically. Numerical aperture of the optical fiber plate 57 is made around 0.6 to 0.8 so that photons directed virtually down can come to the CCD imaging device 82. This increases a measurement accuracy (angle resolution) and image resolution for the distribution of scattered electron. The CCD imaging device 82 used is a device having more than 1 million pixels. The scintillator 81, the optical fiber plate 57, and the CCD imaging device 82 are positioned to obtain a camera length equivalent to higher maximum detection angle than 200 to 300 mrad for the electrons emitted from a specimen. To detect the refracted electrons, the scintillator 81, the optical fiber plate 57, and the CCD imaging device 82 may be positioned aside or above the specimen.

The imaging device control system 83 controls the input and output of the CCD imaging device 82. The imaging device control system 83 controls at what an address a pixel should be activated among more than 1 million pixels. This allows the CCD pixels to be activated in a circular, annular, or other contours so that the electrons from the specimen can be detected in a desired range of angle. The electron intensity information or image information can be obtained with the signal output of the imaging device control system 83 processed as in the first embodiment. Recording and displaying the information should be made as in the first embodiment.

In this embodiment, the present invention provides the electron microscope using a CCD (charge-coupled device) as an imaging device in the electron detection instrument. Therefore this electron detection instrument has wider dynamic range on intensities of incident electron beams than that of embodiment 2. Thus the electron microscope shown in this embodiment is suitable for atomic identification (especially for trace element analysis) at higher accuracy.

[EMBODIMENT 4]

Figure 20:
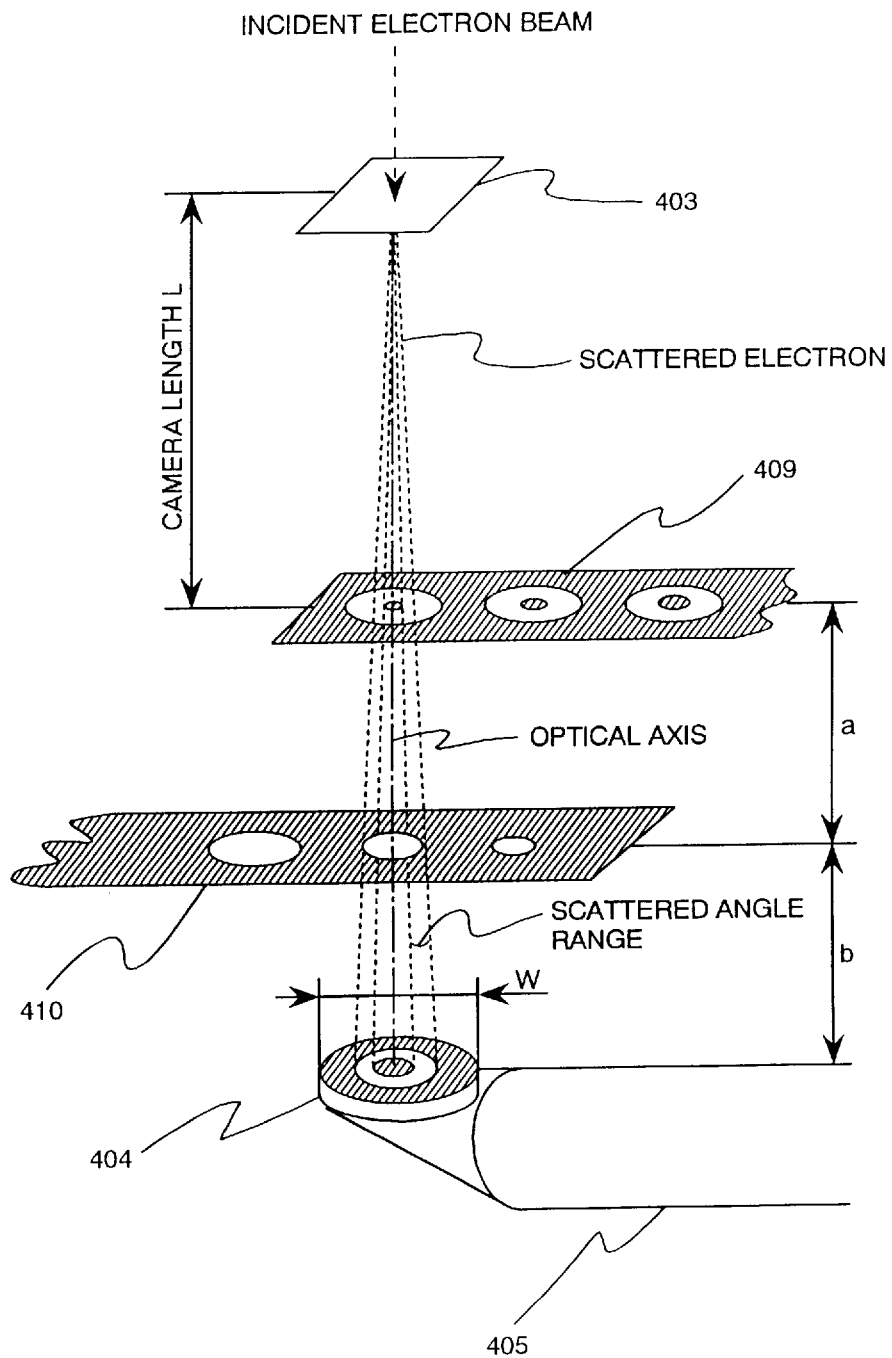
FIG. 20 is an illustration showing the fourth embodiment of the electron detection system of the scanning transmission electron microscope of the present invention.

FIG. 20 is a block diagram of the specimen and electron detection system of the scanning transmission electron microscope used in the fourth embodiment of the present invention.

Differences of the electron detection system of this embodiment from a conventional example are that a scattering angle limiting aperture (for the inner angle) 409 and a scattering angle limiting aperture (for the outer angle) 410 are installed between a specimen 403 and an electron detector (comprising a scintillator 404 and a light guide 405) and only one electron detector is installed. The scattering angle limiting aperture (for the inner angle) 409 and the scattering angle limiting aperture (for the outer angle) 410 set the inner and outer angles within the scattering angle range of scattered electrons used for imaging respectively. Each of the scattering angle limiting apertures is a thin plate ten to several hundreds um in thickness (the material is, for example, Mo) having a plurality of openings, and the openings of the inner angle limiting aperture 409 have a doughnut shape, and the openings of the outer angle limiting aperture 410 are circular. The openings are processed by machining, chemical polishing by photoengraving, or electric sparking according to the plate thickness and opening diameter.

Figure 21:
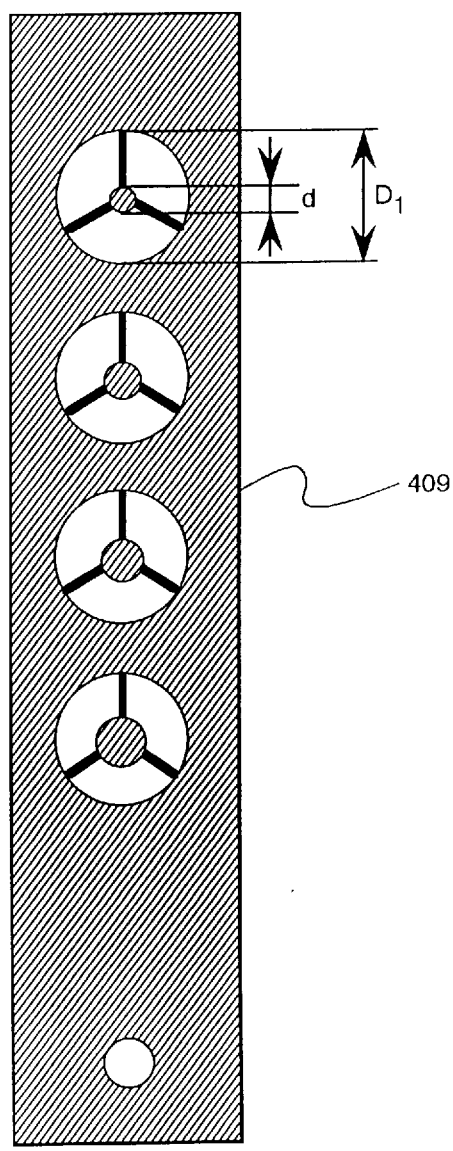
FIG. 21 is a plan view of the scattering angle limiting aperture (for the inner angle) of the present invention.

The detailed shape of the scattering angle limiting aperture (for the inner angle) 409 is shown in FIG. 21. This embodiment shows a case that there are 4 openings provided. Each opening has a bridge for supporting a circular thin plate at the center thereof. The lower end portion of the thin plate shown in the drawing has a screw hole for fixing the thin plate. With respect to the inner diameter d and the outer diameter D1 of the openings, for example, d is set to 0.5, 1.5, 3.0, and 5.0 mm respectively and D1 is set to 10 mm for all the openings. The bridge width is set to, for example, 10% of the minimum inner diameter d or less. The detailed shape of the scattering angle limiting aperture (for the outer angle) 410 is not shown in the drawing, though a difference from the scattering angle limiting aperture (for the inner angle) 409 is only that the openings are circular. When four openings are provided, the diameter $D_2$ of each opening is set to, for example, 2.5, 5.0, 7.5, and 8.75 mm respectively.

The scintillator 404 at the tip of the electron detector shown in FIG. 20 converts the scattered and transmitted electron intensities from a specimen to light intensities and uses crystalline powder or a single crystal plate of ZnS doped with Cd, S, or Ag or YSO doped with Ce. The shape is circular and the whole surface is a scintillator. The center of the scintillator 404 coincides with the optical axis.

Conditions of the scintillator 404 are that the luminescence output is large, and the degradation is little, and the luminescence damping time is short for an electron beam having energy equivalent to the acceleration voltage (100 to 300 kV) of the scanning transmission electron microscope. The aforementioned materials satisfy the conditions. The thickness of the scintillator 404 is set to tens to hundreds um so as to suppress absorption of generated light in the scintillator. An Al film tens nm in thickness is evaporated onto the surface so as to prevent charge up.

How the scattering angle range of scattered electrons to be set on the scintillator 404 is decided when the scattering angle limiting apertures for the inner and outer angles 409 and 410 are used will be explained hereunder with reference to FIG. 20. The space between the specimen 403 and the scattering angle limiting aperture (for the inner angle) 409 is set to the camera length L, and the space between the scattering angle limiting aperture (for the inner angle) 409 and the scattering angle limiting aperture (for the outer angle) 410 is assumed as a, and the space between the scattering angle limiting aperture (for the outer angle) 410 and the scintillator 404 is assumed as b, and the diameter of the scintillator 404 is assumed as W. In this embodiment, L=25 mm, a=0.5 mm, b=25 mm, and W=20 mm.

The maximum angle of scattered electrons which can be detected by the scintillator 404 is the quotient obtained by dividing the radius of the scintillator 404 by the space between the specimen and the scintillator 404, that is, 10/(25+0.5+25)=about 0.2 rad. In the same way, the scattering angle of scattered electrons passing through the openings of the scattering angle limiting aperture (for the inner angle) 409 is the quotient obtained by dividing ½ of the inner diameter of the openings (d/2) by L on the inside and the quotient obtained by dividing ½ of the outer diameter of the openings ($D_1$/2) by L on the outside. When the opening diameter d=0.5, 1.5, 3.0, and 5.0 mm and $D_1$=10 mm as explained in FIG. 21, the scattering angle is 10, 30, 60, and 100 mrad on the inside and 200 mrad on the outside (coincides with the maximum detection angle of the scintillator 404). In the same way, the scattering angle of scattered electrons passing through the openings of the scattering angle limiting aperture (for the outer angle) 410 on the outside is 50, 100, 150, and 175 mrad when the opening diameter $D_2$=2.5, 5.0, 7.5, and 8.75 mm. Therefore, by setting one of 4 kinds of openings of each of the scattering angle limiting aperture (for the inner angle) 409 and the scattering angle limiting aperture (for the outer angle) 410 to the optical axis, various scattering angle ranges can be set. In this case, it is possible to remove the scattering angle limiting aperture (for the outer angle) 410 from the optical axis and use only the scattering angle limiting aperture (for the inner angle) 409. If only the scattering angle limiting aperture (for the outer angle) 410 is used inversely, a bright-field image in which transmitted electrons and scattered electrons are detected at the same time can be observed. To observe a bright-field image (for example, the scattering angle is less than 5 mrad) in which the contribution of scattered electrons is reduced, it is desirable to decrease the opening diameter of the scattering angle limiting aperture (for the outer angle) 410 (for example, $D_1$=0.25 mm).

When this embodiment is used, scattered electrons can be detected in various scattering angle ranges, so that imaging using the desired angle range among the angle distribution of scattered electron intensity is made possible. By doing this, an electron microscope image in which a specific element among the elements constituting a specimen is contrast-emphasized can be observed and furthermore, from comparison of quantitative determination of contrast and contrast calculation using the electron scattering theory, the atomic number Z can be determined, that is, the atomic species can be determined.

[EMBODIMENT 5]

Figure 22:
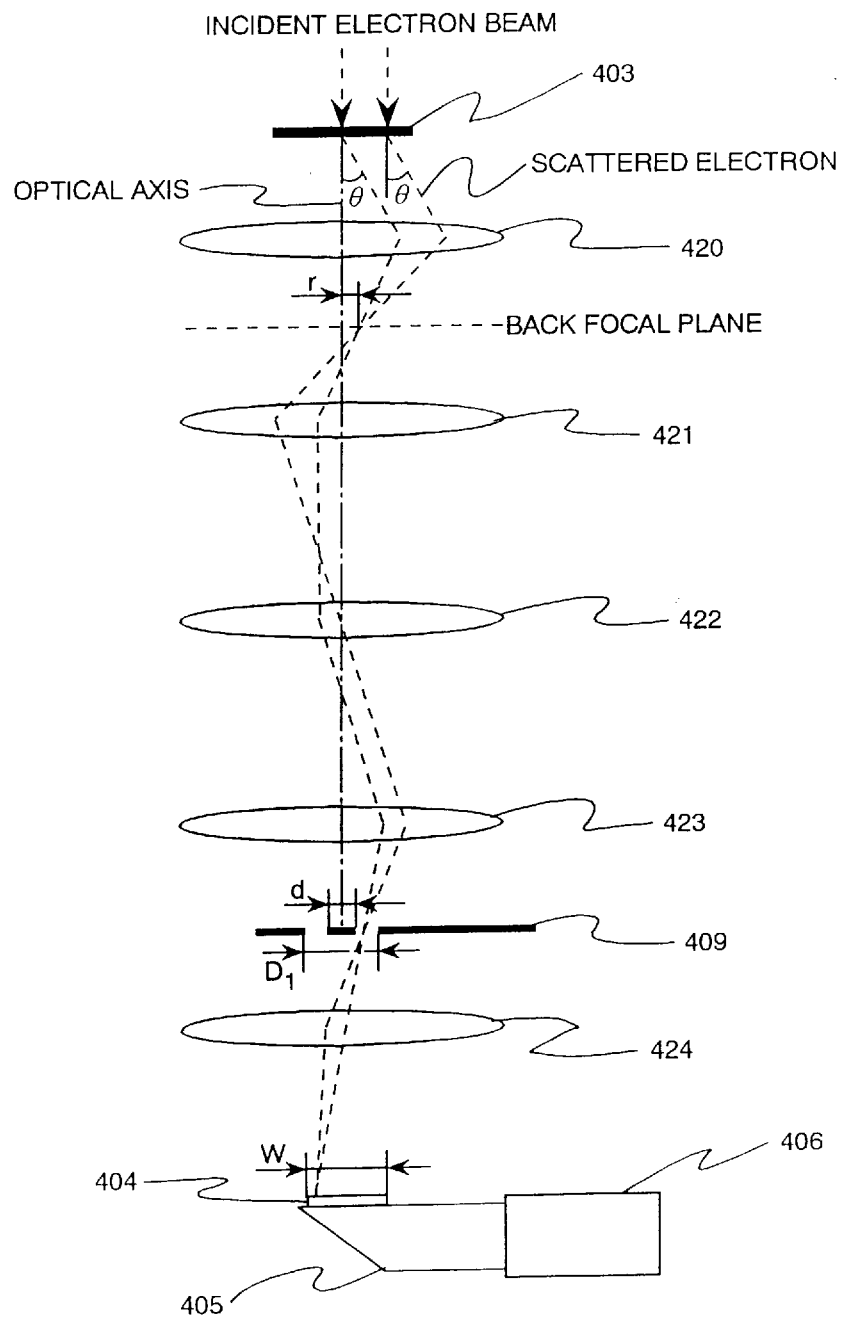
FIG. 22 is a drawing showing the fifth embodiment of the electron detection system of the scanning transmission electron microscope of the present invention.

FIG. 22 is a block diagram of the specimen, imaging lens system, and electron detection system of the scanning transmission electron microscope used in the fifth embodiment of the present invention. The electron illumination system, electron scanning system, and image display unit which are not shown in this drawing are the same in the constitution and imaging operation as those of the fourth embodiment. Differences from the fourth embodiment are that an imaging lens system (comprising an object lens 420, a first intermediate lens 421, a second intermediate lens 422, a first projection lens 423, and a second projection lens 424) is installed between a specimen 403 and an electron detector (comprising a scintillator 404, a light guide 405, and a photomultiplier 406) and only one scattering angle limiting aperture (for the inner angle) 409 is installed as a aperture for limiting the scattering angle range of scattered electrons used for imaging. The installation position of the scattering angle limiting aperture (for the inner angle) 409 is between the first projection lens 423 and the second projection lens 424 in FIG. 22. However, it may be installed between any lenses of the imaging lens system.

Characteristics of this embodiment are that since the camera length L shown in FIG. 20 can be changed optionally by enlarging or reducing the image magnification by changing the exciting current of the imaging lens system, the outside scattering angle can be changed even if the scattering angle limiting aperture (for the outer angle) 410 is not provided and the inside scattering angle can be changed without being limited by the inner diameter of the openings of the scattering angle limiting aperture (for the inner angle) 409.

How the scattering angle range of scattered electrons to be set on the scintillator 404 is decided in this embodiment will be explained hereunder with reference to FIG. 22. It is assumed that the focal length F of the object lens 420 is 2.3 mm, and the four kinds of inner diameters d of the openings of the scattering angle limiting aperture (for the inner angle) 409 is 0.23, 0.26, 0.31, and 0.46 mm, and the outer diameter $D_1$ of the openings is 1.55 mm, and the diameter W of the scintillator 404 is 20 mm. It is also assumed that the magnification of the imaging lens system at the position of the scattering angle limiting aperture is $M_1$ and the magnification of all the imaging lenses on the scintillator 404 is $M_2$.

As shown in the drawing, electrons scattered from the specimen at the same angle are imaged at one point on the back focal face by the object lens 420 regardless of the emission position on the specimen. In this case, the distance r from the optical axis to the imaging point is equal to the product of the scattering angle θ and the focal length F. The image formed on the back focal face is enlarged or reduced by the imaging lenses behind the first intermediate lens 421 and focused on the scattering angle limiting aperture (for the inner angle) 409 and the scintillator 404. Therefore, the distance r to the imaging point corresponding to θ becomes $rM_1$ on the scattering angle limiting aperture (for the inner angle) 409 and $rM_2$ on the scintillator 404. Therefore, when $M_1$=1.67 and the opening diameter of the scattering angle limiting aperture (for the inner angle) 409 is as mentioned above, the inside scattering angles are 30, 34, 40, and 60 mrad and the outside scattering angle is 200 mrad.

In this embodiment, when $M_1$=1.67, $M_2$=21.7. Therefore, r (diameter) for θ=200 mrad becomes 10 mm on the scintillator 404 and coincides with W (diameter)=200 mm set above. When $M_1$ is set to 3.38 and $M_2$ is set to 43.93 by changing the exciting current of the imaging lens system, the inside scattering angles become 15, 17, 20, and 30 mrad and the outside scattering angle becomes 100 mrad. In the same way as with Embodiment 4, θ=100 mrad coincides with W. As mentioned above, with respect to the scattering angle range detected on the scintillator 404, the inside scattering angle depends on the magnification of the imaging lens system on the specimen side from the position where the scattering angle limiting aperture is installed up to the position of the scattering angle limiting aperture, the focal length of the object lens, and the inner diameter of the doughnut-shaped openings. The outside scattering angle depends on the magnification of all the imaging lenses at the position of the electron detector, the focal length of the object lens, and the diameter of the detection face of the electron detector.

On the other hand, to observe a bright-field image, the scattering angle limiting aperture (for the inner angle) 409 is removed from the optical axis and the magnification $M_2$ of all the imaging lenses on the scintillator 404 is increased. For example, to form an image by transmitted electrons and scattered electrons within a scattering angle θ of 4 mrad, it is desirable to set $M_2$ to 1102. All the values of $M_1$ and $M_2$ described in this embodiment can be realized by the lens constitution shown in FIG. 22.

Another characteristic of this embodiment is that if an incident electron beam is illuminated in parallel without scanning by changing the operation conditions of the illumination lens system, a transmission electron microscope image can be observed. In this case, by removing the scattering angle limiting aperture (for the inner angle) 409 and the electron detector from the optical axis and controlling the exciting conditions of the imaging lens system, not only a diffracted image formed on the back focal plane of the object lens 420 but also a real image formed on the image plane can be observed. The fluorescent screen, film, and electron microscope TV camera installed under the imaging lens system are used to observe and record an image.

a 2-dimensional projection image 113, a process of obtaining a plurality of 2-dimensional projection images 113 observed in various directions by tilting a thin film specimen 112 around a certain tilt axis 114, a process of identifying the tilt axis 114 from the plurality of 2-dimensional projection images 113 by image analysis, a process of setting the tilt axis 114 according to the design specification, a process of constructing 2-dimensional cross-sectional images 101 crossing the plurality of 2-dimensional projection images 113 at right angles from the projection images, and a process of analyzing a 3-dimensional atomic arrangement image from a 3-dimensional image constructed by piling the 2-dimensional cross-sectional images 101. Each process will be explained hereunder in detail.

The specimen 112 is rotated around the tilt axis 114 by using the specimen tiling system 108 and a plurality of 2-dimensional projection images 113 observed in various directions are obtained.

Figure 26:
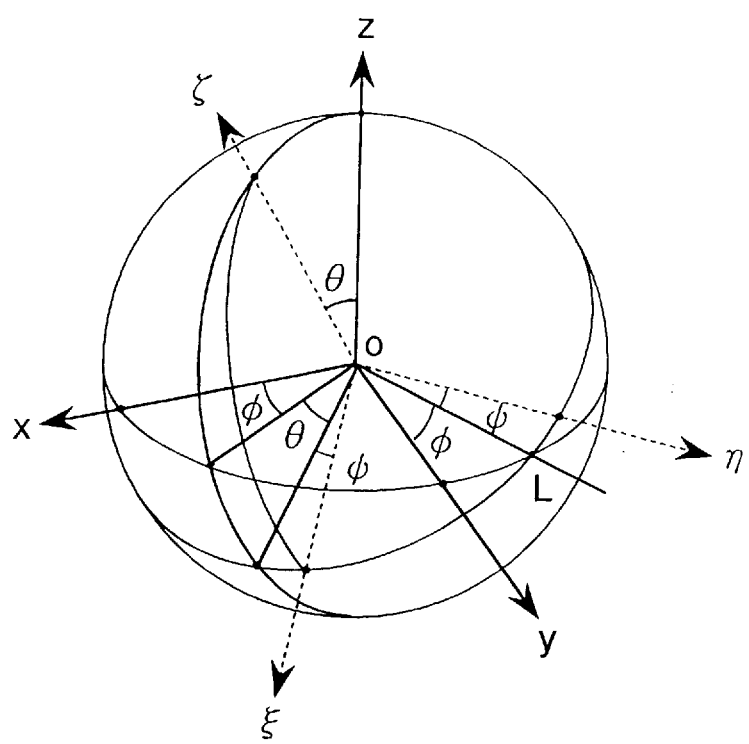
FIG. 26 is an illustration showing the relation between the coordinate system xyz, the coordinate system ξηζ, and the Euler angles θφϕ.

Next, the process of identifying the tilt axis 114 from the plurality of 2-dimensional projection images 113 by image analysis will be described. The coordinate systems shown in FIG. 26 are assumed. The orthogonal coordinate system fixed to the observation system is assumed as a coordinate system xyz and the orthogonal coordinate system fixed to the specimen 112 is assumed as a coordinate system ξηζ. The coordinate conversion between the coordinate system xyz and the coordinate system ξηζ is expressed by the following equation using the Euler angles θ, φ, and ϕ.

$$\begin{bmatrix} \xi \\ \eta \\ \zeta \end{bmatrix} = \begin{bmatrix} \cos\psi\cos\phi & \cos\theta - \sin\psi\sin\phi\cos\psi & \sin\phi\cos\theta + \sin\psi\cos\phi & -\cos\psi\sin\theta \\ \sin\psi\cos\phi & \cos\theta - \cos\psi\sin\phi\sin\psi & \sin\phi\cos\theta + \cos\psi\cos\phi & \sin\psi\sin\theta \\ \cos\psi & \sin\theta & \sin\psi\sin\theta & \cos\theta \end{bmatrix} \begin{bmatrix} x \\ y \\ z \end{bmatrix} \quad \text{Equation 1}$$

According to the present invention, a scanning transmission electron microscope for detecting the scattering angle distribution of electron intensity scattered and transmitted in a specimen within the desired angle range and observing the internal structure of the specimen by a simple equipment constitution can be provided.

[EMBODIMENT 6]

Figure 23A:
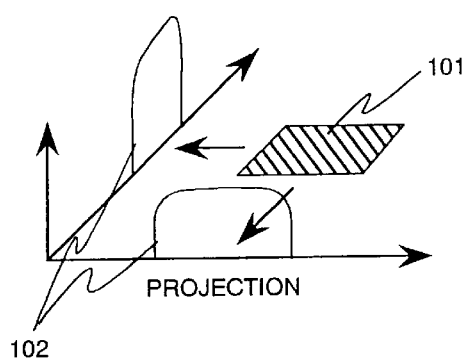
FIG. 23A is an illustration showing the principle of image reconstruction by projection and FIG. 23B is an illustration showing the principle of image reconstruction by back projection.
Figure 23B:
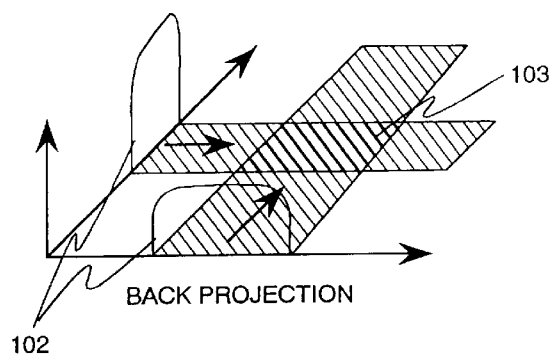

Image restructure is processing of recording projection data 102 in various directions of a 2-dimensional cross-sectional image 101 of an object intuitively as shown in FIGS. 23A and 23B and reconstructing a 2-dimensional reconstructed image 103 by projecting the projection data inversely. If the 2-dimensional reconstructed image 103 matches the 2-dimensional cross-sectional image 101, it may be said that the original image is restored perfectly. The present invention provides a method of clarifying observation conditions and processes necessary to apply the aforementioned image reconstructed method to an electron microscope image actually observed and satisfying the conditions.

Figure 24:
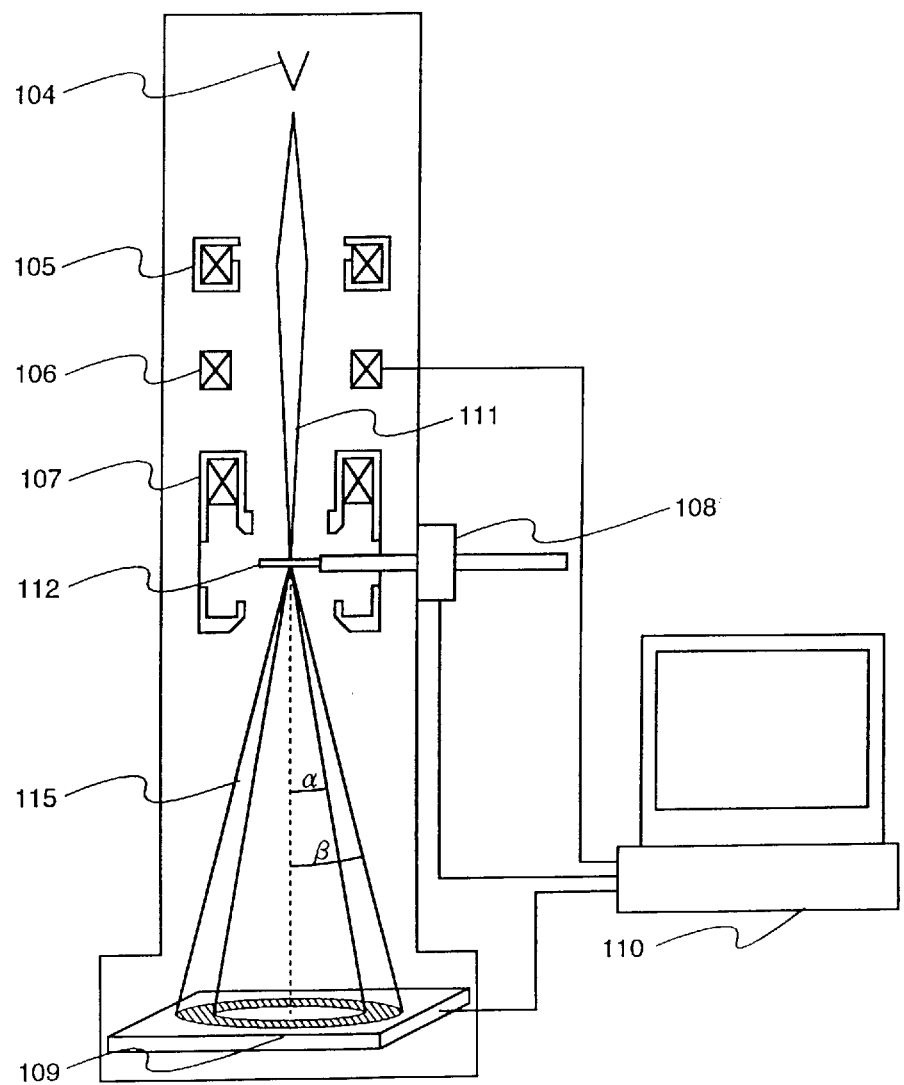
FIG. 24 is a whole block diagram of the equipment used in the embodiments of the present invention.
Figure 25:
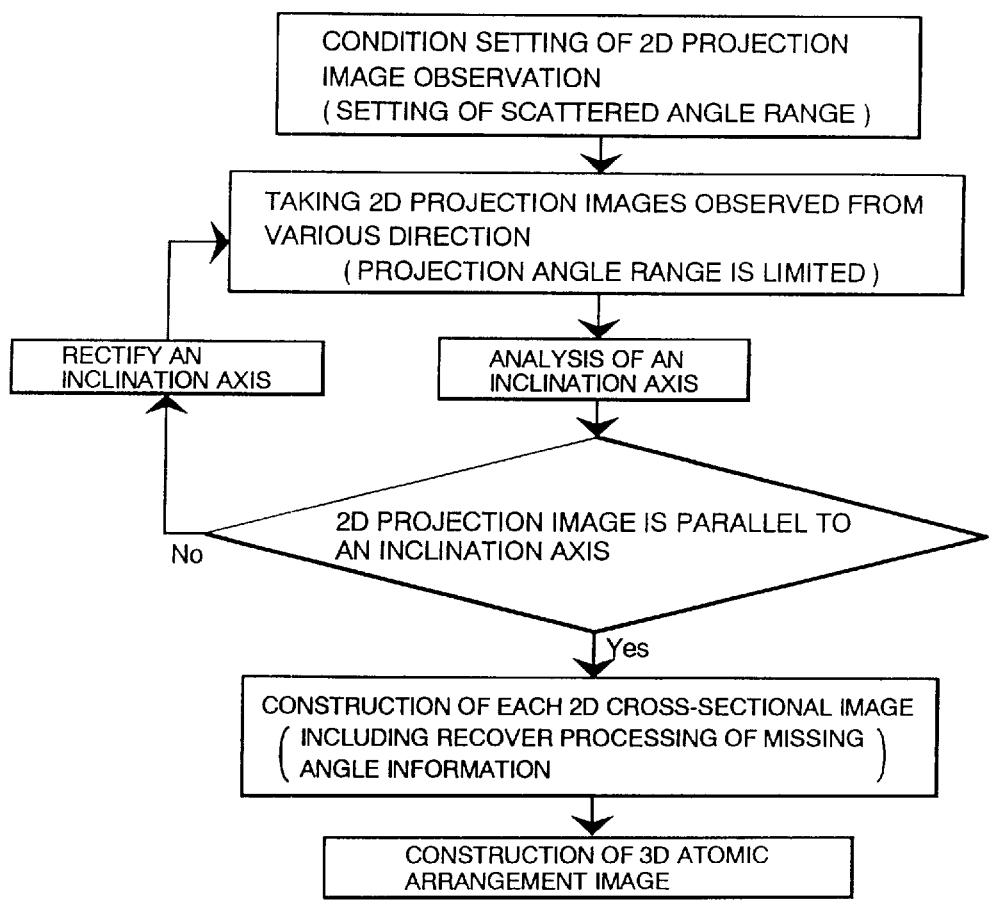
FIG. 25 is a flow chart showing the processes for constructing a 3-dimensional atomic arrangement image.
Figure 27:
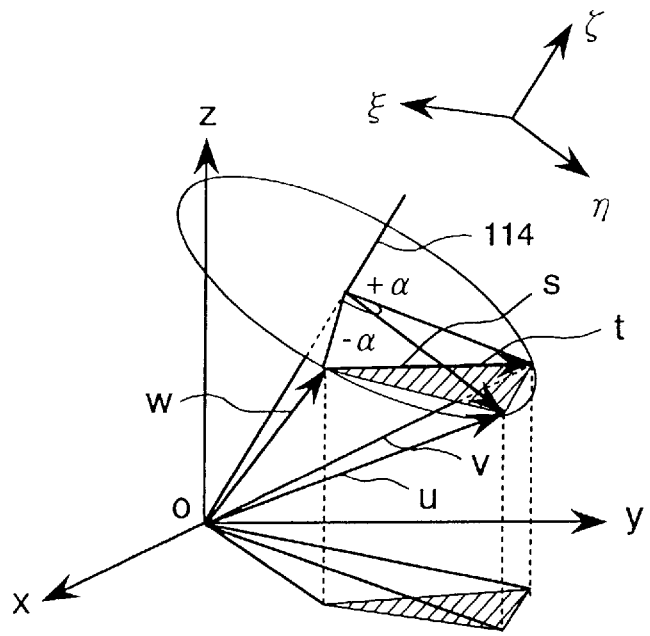
FIG. 27 is an illustration showing each vector used for analysis of the coordinate systems.

FIG. 24 shows the basic constitution of the electron microscope used in the embodiments of the present invention. The electron microscope comprises a field emission electron gun 104, a capacitor lens 105, a deflecting and scanning coil for electron beam 106, an object lens 107, a specimen goniometer tiling system 108, an electron detector 109, and a processor for control and image processing 110. FIG. 25 is a flow chart showing the processes for constructing a 3-dimensional atomic arrangement image. The processes include a process of setting observation conditions of When a standard specimen whose shape is known is used, the Euler angles θ, φ, and ϕ can be obtained from correspondence between the value of (ξηζ) set by the specimen system and the value of (xyz) measured by the measurement system when the specimen is tilted around the tilt axis. However, a structure that the shape is known is not included generally in TEM specimens. Therefore, an optional characteristic point in the specimen 112, for example, an Ag atom in a crystal of Si is used. Two characteristic points are selected from the specimen and a vector linking the two points is used for analysis. As shown in FIG. 27, the tilt axis 114 is assumed as a ζ axis and the specimen 112 is rotated around the ζ axis. The vector when the specimen 112 is not rotated is assumed as u, and the vector when the specimen 112 is rotated around the ζ axis in a +α arc is assumed as v, and the vector when the specimen 112 is rotated around the ζ axis in a −α arc is assumed as w. On the coordinate system ξηζ, the vectors u, v, and w form an isosceles triangle on the ξη plane. The vector s=v−w is parallel with the ξ axis and the vector t=u−(v+w)/2 is parallel with the η axis. The length ratio of the two vectors can be obtained from the rotational angle α, so that a unit vector of the coordinate system ξηζ, vector s'=(k, 0, 0), and vector t'=(0, k, 0) can be set. The Euler angles θ, φ, and ϕ and the length k of the unit vector can be obtained from the correspondence between the values of the vectors s' and t' obtained by measuring the coordinates of the vectors u, v, and w on the observation system xyz and the values of the vectors s' and t' on the ξηζ coordinate system and the direction of the ζ axis which is the tilt axis 114 can be analyzed. The z coordinate of the observation system cannot be measured because a projection image in the z direction is observed. However, since four simultaneous equations can be defined by the x and y coordinates of the vector s' and the x and y coordinates of the vector t', four variables can be identified.

By the aforementioned process, even if a specimen whose shape is known is not used, the tilt axis 114 can be analyzed by image analysis using characteristic points in the specimen. To avoid a reading error, two points in the specimen are selected so that the lengths of the vectors s and t are made as long as possible. To make the difference in length between the vectors s and t smaller, it is desirable to make the rotational angle δ as large as possible. It is desirable that a characteristic point is shaped so that the position thereof can be identified by observation in any direction, for example, it is a particle or a vertex of a rectangular parallelepiped. When there exists no suitable characteristic point in the specimen, a focused electron beam is illuminated to a square of notable area and a characteristic point, for example, a defect or contamination mark is prepared.

Figure 28:
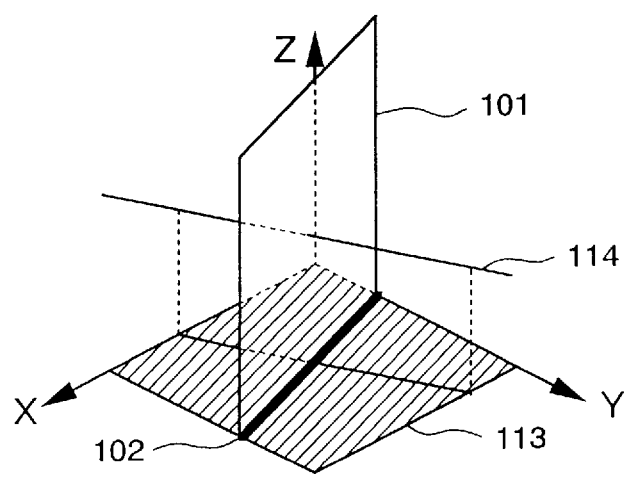
FIG. 28 is an illustration showing that 1-dimensional projection data can be acquired from a 2-dimensional projection image when the tilt axis is parallel to the 2-dimensional projection image.

Next, the process of setting the tilt axis 114 according to the design specification will be described. Firstly, the design specification of the tilt axis is shown in FIG. 28. When the 2-dimensional projection image 113 is observed in the z direction, if the tilt axis 114 is parallel with the xy plane which is a projection image plane, a line profile crossing the tilt axis 114 at right angles which is reflected on the 2-dimensional projection image 113 becomes the 1-dimensional projection data 102 of the 2-dimensional cross-sectional image 101. The tilt axis 114 is set so that it is parallel with the xy plane using the specimen tilting system 108 and it is checked whether the direction of the tilt axis satisfies the design specification using the aforementioned tilt axis analytical method. When the direction of the tilt axis does not satisfy the design specification, it is corrected by using the specimen tilting system.

Next, the processes of constructing each 2-dimensional cross-sectional image will be described. The processes include a process of acquiring 1-dimensional projection data of 2-dimensional cross-sectional images crossing a plurality of 2-dimensional projection images 113 observed by tilting around the tilt axis 114 set in the direction of the design specification at right angles from the projection images, a process of constructing 2-dimensional reconstructed images by projecting the 1-dimensional projection data inversely, a process of deleting an area where 2-dimensional cross-sectional images cannot be restored from the 2-dimensional reconstructed images, and a process of obtaining 2-dimensional cross-sectional images by performing the lacking angle information recovery process to the 2-dimensional images.

Figure 29A:
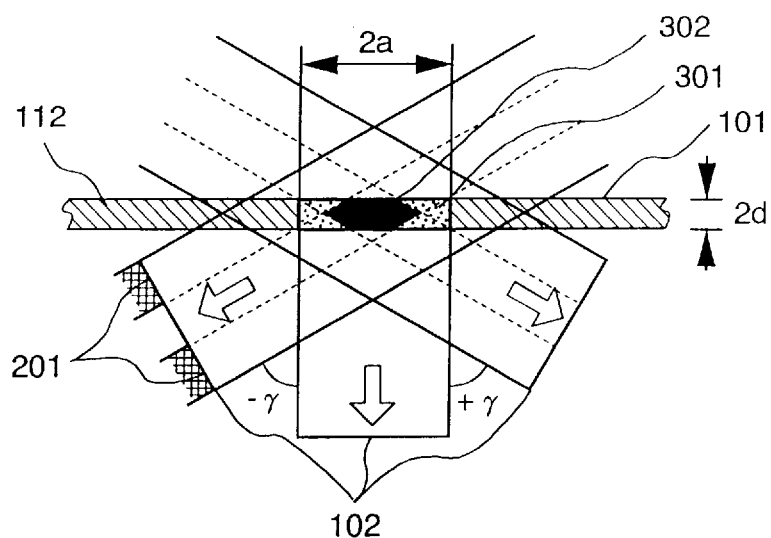
FIG. 29A is an illustration showing the relation between 1-dimensional projection data and a 2-dimensional cross-sectional image when a specimen is thin and FIG. 29B is an illustration showing the relation between 1-dimensional projection data and a 2-dimensional cross-sectional image when a specimen is thick.
Figure 29B:
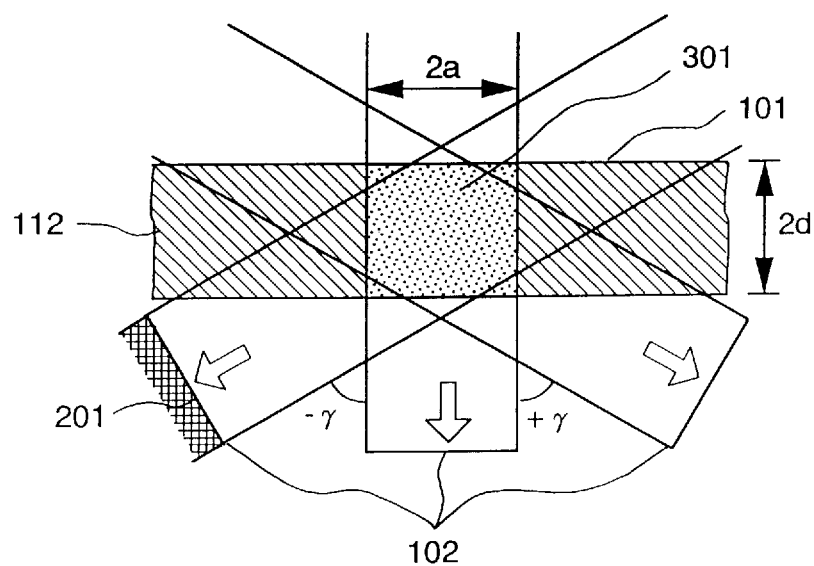

The process of acquiring 1-dimensional projection data will be described hereunder. Firstly, the geometric relations of the 1-dimensional projection data 102 and the 2-dimensional cross-sectional image 101 are shown in FIGS. 29A and 29B. The specimen 11 is assumed as a flat specimen $2d$ in thickness. A notable area 301 is set in the specimen 112 and the width thereof is assumed as $2a$. The maximum tilt angle of the specimen 112 is assumed as $\pm\gamma$ degrees. Firstly, a case that d is sufficiently smaller than a as shown in FIG. 29A will be considered. In data 201 at both ends of the 1-dimensional projection data 102 at the specimen tilt angle γ, projection data in an area other than the notable area 301 coexists. Therefore, only the 1-dimensional projection data 102 from which the both-end data 201 is deleted is used for image restructure. Several methods for deciding the range of the both-end data 201 will be described hereunder. The range to be deleted is $a(1-\cos\gamma)-2d\cdot\sin\gamma$ from both ends of the data from the geometric relation. If a characteristic point exists around the notable area 301 though the thickness $2d$ of the specimen 112 is not known, the range can be decided from the position of the characteristic point on the projection data. If no characteristic point exists around the notable area 301, a focused electron beam is illuminated to the square of notable area and a characteristic point, for example, a defect or contamination mark is prepared and the range is decided from the position of the characteristic point on the projection data. When d and a are almost the same in length as shown in FIG. 29B, projection data in an area other than the notable area 301 coexists in the whole range of the 1-dimensional projection data 102 at the specimen tilt angle γ and it is found that the 1-dimensional projection data 102 cannot be used for the reconstruction process. Therefore, it is necessary to set the width $2a$ of the notable area 301 as wide as possible.

Next, the process of constructing 2-dimensional reconstructed images by projecting the 1-dimensional projection data inversely is executed by the 2-dimensional Fourier conversion method used by general X-ray-CT, the filter correction inverse projection method, or the superimposed integral method.

Next, the process of deleting an area where 2-dimensional cross-sectional images cannot be restored from the 2-dimensional reconstructured images will be described. In the 2-dimensional reconstructed image when the 1-dimensional projection data 102 is projected inversely, the area inversely projected from the projection data at all the specimen tilt angles is only an area 302 among the notable area 301 shown in FIG. 29a. In the area other than the area 302, the information amount of projection data included in the image is extremely little. The projection angle range is limited in an electron microscope, so that it is necessary to execute a suitable lacking angle information recovery process using the known information. However, if this process is applied to the notable area 301 at it is, not only a cross-sectional image in an area other than the area 302 cannot be recovered but also the area other than the area 302 may cause an artifact in the restorable area 302. Therefore, it is necessary to delete the area other than the area 302 and replace it with a suitable specimen structure, for example, a substrate crystal so as to prevent an artifact. The area other than the area 302 can be geometrically identified, when a straight line is drawn in each projection direction from the end of the notable structure, as an area outside it.

Next, the process of obtaining 2-dimensional cross-sectional images by performing the lacking angle information recovery process to the processed 2-dimensional images 103. The lacking angle information recovery process is executed on the basis of the known information on 2-dimensional cross-sectional images, for example, probability information and symmetry.

Next, the process of analyzing a 3-dimensional atomic arrangement and an atomic species from a 3-dimensional image constructed by piling the 2-dimensional cross-sectional images 101 will be described. Each 2-dimensional cross-sectional image is sequentially reconstructed along the specimen tilt axis and a 3-dimensional structure is constructed by piling them. The image contrast of the 2-dimensional projection image 103 depends on the number of atoms existing on the path through which the electron beam passes and the atomic number Z thereof, so that it is difficult to identify the atomic number Z only from the the 2-dimensional projection image 103. By analyzing the specimen shape by 3-dimensional restructure, the atomic number Z of atoms constituting the specimen can be identified.

According to the present invention, a 3-dimensional atomic arrangement image can be structured with high precision from an electron microscope image observed in various directions using the general image reconstruction theory. By doing this, impure atoms in a crystal and the 3-dimensional structure of the cluster thereof can be analyzed on a level of an atom. Therefore, information valid in analysis of defect causes of the ULSI aperture such as a leakage current or a poor voltage resistance is provided.

[EMBODIMENT 7]

An embodiment of the present invention will be explained hereunder with reference to the drawings and expressions.

Figure 30:
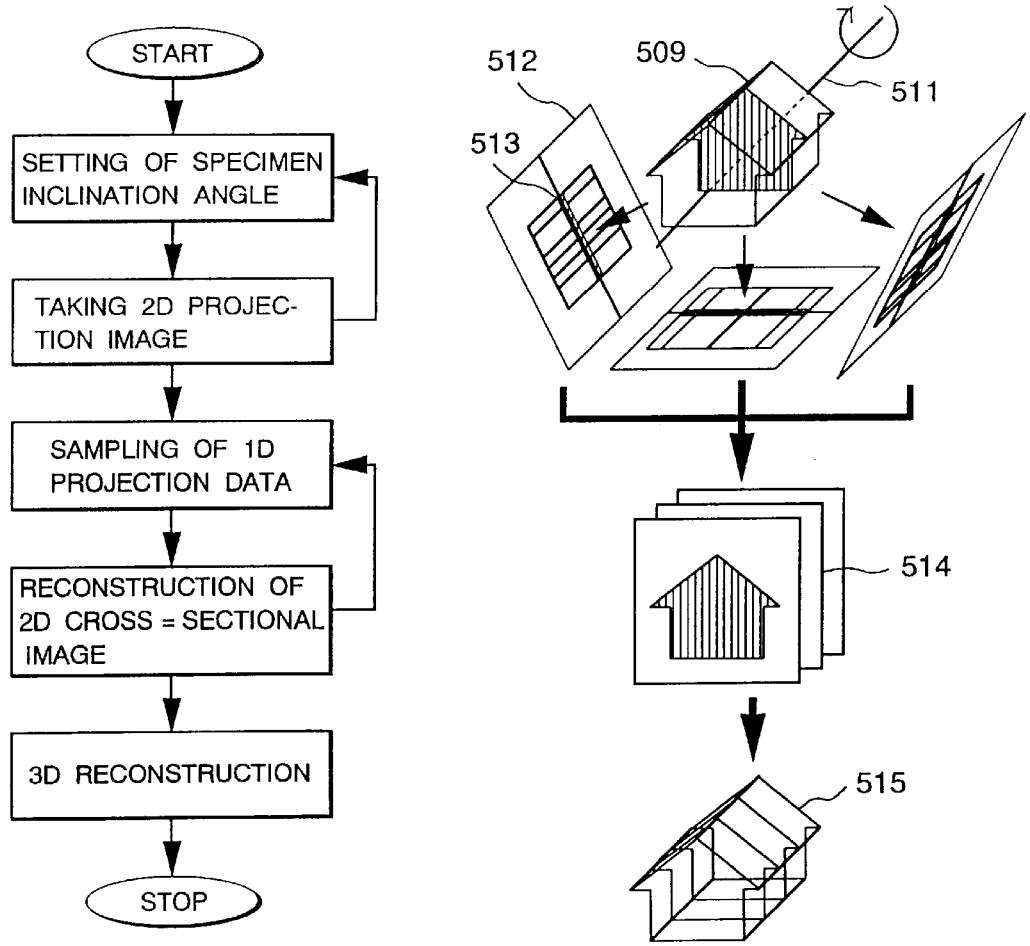
FIG. 30 is a flow chart showing the constitution for constructing a 3-dimensional structure.

FIG. 30 is a flow chart showing the processes of constructing a 3-dimensional structure. The processes include a process of obtaining 2-dimensional projection images in various directions by tilting a thin film specimen around the specimen tilt axis, a process of acquiring 1-dimensional projection data of 2-dimensional cross-sectional images crossing the plurality of 2-dimensional projection images at right angles from the projection images, a process of reconstructing the 2-dimensional cross-section from the -dimensional projection data, and a process of constructing a 3-dimensional structure by piling the 2-dimensional cross-sectional images.

The present invention is characterized in that the process of reconstructing the 2-dimensional cross section from the 1-dimensional projection data uses the algebraic method as an image restructure method.

Firstly, the algebraic method will be explained. The M-dimensional vector generated from values at N standard points on a certain 2-dimensional cross-sectional image is assumed as f, and the N-dimensional vector generated from projection thereof is assumed as g, and the relation between the two is expressed by g=[R]f. [R] indicates an M by N matrix. The algebraic method is a method for obtaining f from g on the basis of this relation.

Figure 31A:
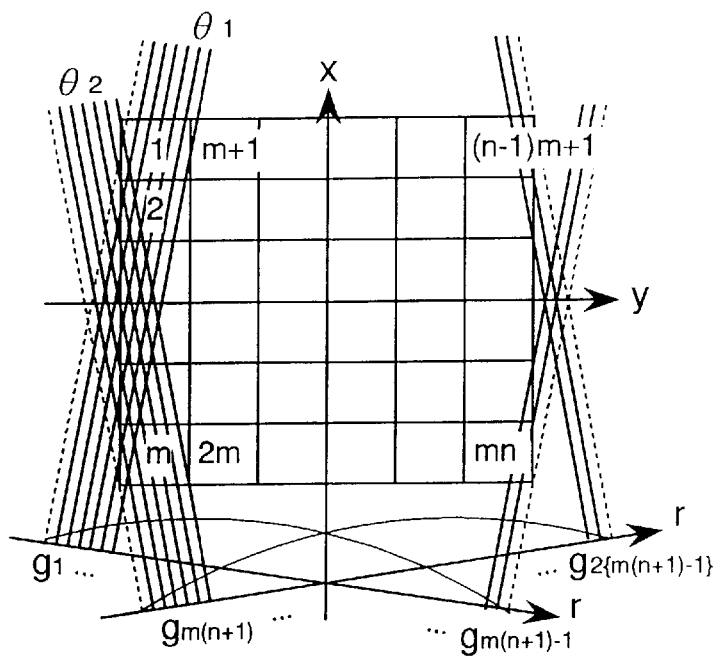
FIGS. 31A and 31B are illustrations for the image reconstruction method from projection images in the four directions.
Figure 31B:
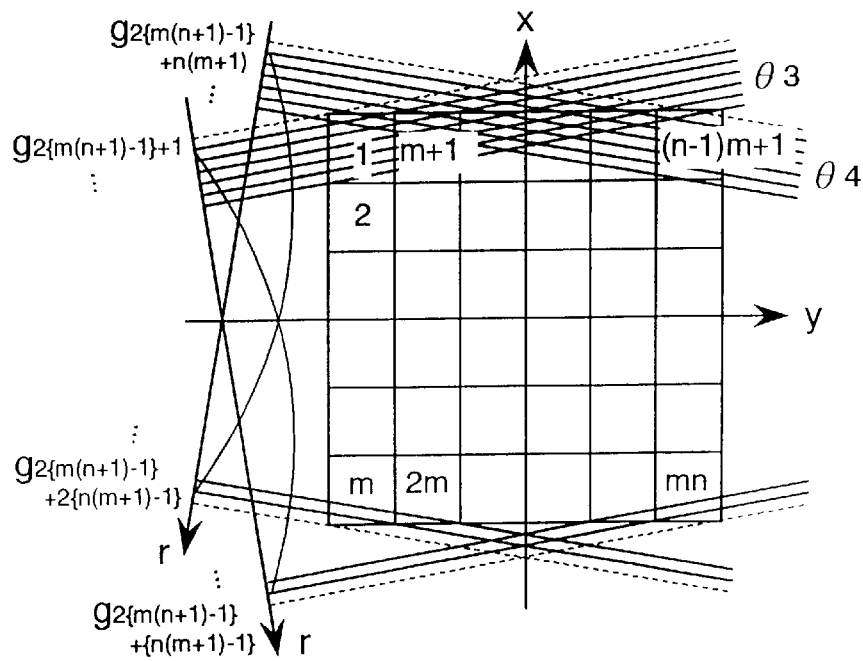

In the algebraic method, how to set the projection system [R] poses problems. In this embodiment, the following projection system [R] is set as an image restructure method from projection in a small number of directions. Firstly, an original image is assumed as a 2-dimensional cross-sectional image on the xy orthogonal coordinate system, and the original image is divided into m pixels in the x direction and n pixels in the y direction, and each pixel is numbered in the order shown in FIGS. 31A and 31B, and the intensity of each pixel, that is, the electron scattering factor $f_j$ is placed in a row and the row is assumed as f. m×n is assumed as M. Projection data $g_i$ is expressed by the following expression.

$$g_i = \sum_{i=1}^{M} R_{ij}f \quad (i = 1, 2, \ldots, N) \quad \text{Equation 1}$$

where $R_{ij}$ indicates a length through which an electron beam generating the projection data $g_i$ passes pixels having the electron scattering factor $f_j$. Projection data g is generated by placing each projection data in the directions $\theta_1$ to $\theta_4$ shown in FIGS. 31A and 31B in a row. The four directions $\theta_1$ to $\theta_4$ are four directions of the directions at angles of $+\theta_m$ and $-\theta_m$ with the x axis and the directions at angles of $+\theta_n$ and $-\theta_n$ with the y axis. In this case, tan $\theta_m$=1/m and tan $\theta_n$=1/n.

Since M<N in this projection system [R], the least square solution satisfying the measured g is f. Whether the cross-sectional image f can be reconstructed accurately from the projection g by the projection system [R] or not can be estimated by calculating the order or norm of [R]. The result shows that the cross-sectional image f can be reconstructed sufficiently. Simulation verification of projecting an original image of 128 by 128 pixels and reconstructing a cross-sectional image from this projection is executed and it is verified that the original image is reconstructed.

As mentioned above, the inner structure is reconstructed only by information of projection in the four directions, so that there is no need to set a supposition in the specimen shape. Therefore, a specimen in an optional shape can be analyzed. The number of projection images necessary for image reconstructure is four, and the electron illumination time for a specimen is shortened, and damage by electron illumination is reduced remarkably, so that also a specimen having worry of electron illustration damage can be analyzed.

Image reconstruction from projection in a small number of directions has the following advantages. In a projection image for image reconstruction, there is a precondition that the electron scattering factor of a specimen and the image contrast have a linear relation. However, when electrons having an equivalent phase among electrons passing through the specimen are used for imaging, the intensity vibrates in the traveling direction of electrons due to mutual interference of electrons. As a result, it is necessary to set observation conditions so that electrons used for imaging have not an equivalent phase.

When an electron beam enters a specimen of a crystal, particularly a single crystal, a number of diffracted waves are generated by the lattice face. For incidence on the crystal zone axis where the electron beam incident direction is parallel with the crystal face, several diffracted waves having a coherent phase are excited dominantly. On the other hand, when observed under the condition that the crystal face is shifted from the electron beam incident direction, diffracted waves having different phases are excited. The prior art requires to obtain a number of projection images at fine intervals of angle for image reconstruction, so that it is necessary to use also projection images observed in crystal zone axis incidence for image reconstruction. To make diffracted waves different in phase also for zone axis incidence, it is necessary that the scattering angle range from $\alpha$ to $\beta$ of electrons used for imaging satisfies the condition that the atomic number Z can be analyzed from the contrast of a 2-dimensional projection image as well as the condition that non-interference thermal diffuse scattering electrons are dominant. However, the scattering angle range within which non-interference thermal diffuse scattering electrons are dominant is considerably higher than the scattering angle range within which the atomic number Z can be analyzed from the image contrast. Namely, the angle range from $\alpha$ to $\beta$ of scattered electrons satisfying both conditions is extremely high, so that the electron intensity is extremely low and when an image is formed by such electrons, it is difficult to observe a clear image. For a specimen in which atoms are apt to be diffracted like a crystal of heavy atoms, even scattered electrons at a considerably high angle are made coherent in phase, so that projection images which can be used for image reconstruction cannot be obtained.

By the aforementioned image processing method, images can be reconstructed by projection images in the aforementioned four directions, so that there is no need to use projection images observed by crystal zone axis incidence. Therefore, it is desirable that the scattering angle range from $\alpha$ to $\beta$ of electrons used for imaging satisfies only the condition that the atomic number Z can be analyzed from the contrast of a 2-dimensional projection image and there is no need to set an extremely high angle like the prior art.

In the algebraic method, f and g are linearly related to each other by the matrix [R], so that the restoration process for preventing noise amplification during image processing can be executed easily.

The restoration process is a process of restoring an original image from an image degraded by the imaging system or noise. An evaluation standard J for measuring whether a restored image f' reconstructs the original image f or not is set and a restored image f' minimizing it is obtained. When the evaluation standard J is in the non-linear relation with f and g, the repetition method of changing f' successively by verifying the evaluation standard J, so that it requires an enormous calculation time. On the other hand, when the evaluation standard J is in the linear relation with f and g, by calculating:

$$\frac{\delta J}{\delta f} = 0 \qquad \text{Equation 2}$$

a restoration filter:

$$f' = [B]g \qquad \text{Equation 3}$$

is obtained. For example, when noise n is included in projection g:

$$g_i = \sum_{i=1}^{M} R_{ij}f_j + n_i \quad (i = 1, 2, \ldots, N) \qquad \text{Equation 4}$$

Assuming the square mean value of noise as $\rho^2$ and the characteristic of the image as $[\Gamma]f$, a filter is designed so that $\|[\Gamma]f\|^2$ is minimized. Namely, assuming:

$$\text{minimize } \|[\Gamma]\|^2 \qquad \text{Equation 5}$$
$$\text{subject to } \|g - [R]f\|^2 = \rho^2$$

the Lagrangean constant $\gamma$ is introduced as an actual evaluation standard J as follows:

$$J = \|[\Gamma]\|^2 + \gamma^{-1}\|g - [R]f\|^2 - \rho^2 \qquad \text{Equation 6}$$

When this is substituted in Equation 2, the restoration filter [B] can be obtained as follows:

$$[B] = ([R]^T[R] + \gamma[\Gamma]^T[\Gamma])^{-1}[R]^T \qquad \text{Equation 7}$$

In image reconstruction of the prior art, the linear relation between f and g is not defined and no restoration filter can be generated, so that only a method of repeating calculation many times so as to obtain f' for minimizing the evaluation standard J like the repetition method can be used. On the other hand, the evaluation standard J can be described in the linear relation using f and g by this method. Therefore, the restoration filter [B] can be generated, and f' minimizing the evaluation standard J can be obtained only by applying the restoration filter [B] to the measured g once, and the calculation time can be reduced greatly.

Finally, the process of constructing a 3-dimensional structure will be explained. A 3-dimensional structure is constructed by piling 2-dimensional cross-sectional images generated by the previous process. The obtained 3-dimensional structure is displayed on the CRT as a bird's-eye view or an optional cross-sectional view depending on the observation object and used to analyze the specimen structure.

In the aforementioned image processing method, if projection images in the aforementioned four directions can be observed, the inner structure can be reconstructed without executing the angle information restoration process on the assumption of the specimen structure. Namely, since there is no need to assume the specimen structure, a specimen in an optional shape can be reconstructed.

In the aforementioned image processing method, the number of projection images, that is, the electron illumination time is very short, so that the specimen deterioration due to electron illumination damage is reduced and a specimen susceptible to electron illumination damage can be analyzed.

There is no need to use a projection image observed by crystal zone axis incidence as a projection image in the aforementioned image processing method, so that the linear relation between the specimen thickness and the image contrast can be kept even if an image cannot be formed by scattered electrons at an extremely high angle. It is sufficient that the scattering angle range of electrons used for imaging is set so that the atomic number Z can be analyzed from the image contrast and a sufficient electron intensity can be obtained, so that a clear projection image can be observed. A specimen which cannot be analyzed by the prior art because electrons are apt to be diffracted like a single crystal of heavy atoms can be analyzed.

In the aforementioned image reconstruction process, a process of suppressing amplification of noise mixed in a projection image can be added easily, so that an accurate specimen structure can be reconstructed even from a projection image including noise, that is, an actually observed projection image.

The present invention uses an electron beam, so that a 3-dimensional structure can be analyzed by a space resolution on the atomic level.

Many different embodiments of the present invention may be constructed without departing from the spirit and scope of the invention. It should be understood that the present invention is not limited to the specific embodiments described in this specification. To the contrary, the present invention is intended to cover various modifications and equivalent arrangements included within the spirit and scope of the claims.

What is claimed is:

1. A scanning electron microscope for imaging by a detected signal, comprising:
    an electron illumination system for focusing an accelerated electron beam and illuminating said electron beam to a specimen on a specimen holder;
    an electron scanning system for scanning said electron beam on said specimen holder; and
    an electron detector for detecting an electron beam from said specimen, wherein said microscope has a limiting aperture having a portion for shielding an electron beam in an opening thereof between said specimen holder and said electron detector, and having an annular shape, and
        wherein further said microscope has, under said limiting aperture, an imaging lens and a lens control portion which can change an exciting current of said imaging lens so as to change image magnification for obtaining an electron beam of a predetermined angle by combining with said limiting aperture.

2. A scanning electron microscope according to claim 1, wherein said limiting aperture comprises at least one plate having a doughnut-shaped opening.

3. A scanning electron microscope according to claim 2, wherein said limiting aperture has a shielding portion in said opening, said opening and said shielding portion are supported by a bridge, and the width of said bridge is narrower than the width of said shielding portion.

4. A scanning electron microscope for imaging by a detected signal, comprising:

an electron illumination system for focusing an accelerated electron beam and illuminating said electron beam to a specimen on a specimen holder;

an electron scanning system for scanning said electron beam on said specimen holder; and an electron detector for detecting an electron beam from said specimen, wherein said microscope has a first limiting aperture and a second limiting aperture between said specimen holder and said electron detector and includes position control means positioned so that openings of said first limiting aperture and said second limiting aperture are partially overlapped with each other.

5. A scanning electron microscope according to claim 4, wherein said first limiting aperture has a shielding portion at a part of said opening thereof and said opening of said second limiting aperture is smaller than said opening of said first limiting aperture and larger than said shielding portion of said first limiting aperture.

6. A scanning electron microscope according to claim 4, wherein said first limiting aperture has a shielding portion in said opening, and said opening and said shielding portion are supported by a bridge, and the width of said bridge is narrower than the width of said shielding portion.

7. A scanning electron microscope according to claim 4, wherein said first limiting aperture is arranged at the specimen holder side and said second limiting aperture is arranged at the electron detector side.

8. A scanning electron microscope according to claim 4, wherein said first limiting aperture has an annular shape.

9. A scanning electron microscope according to claim 4, wherein said first limiting aperture has a round shape.

10. A scanning electron microscope for imaging by a detected signal, comprising:

an electron illumination system for focusing an accelerated electron beam and illuminating said electron beam to a specimen on a specimen holder;

an electron scanning system for scanning said electron beam on said specimen holder; and an electron detector for detecting an electron beam from said specimen, wherein said microscope has a limiting aperture, having an annular shape, between said specimen holder and said electron detector, and an imaging lens and a lens control portion, which can change an exciting current of said imaging lens so as to chance image magnification for obtaining an electron beam of a predetermined angle by combining with said limiting aperture, are arranged between said limiting aperture and said electron detector.

11. A scanning electron microscope according to claim 10, wherein said limiting aperture has a shielding portion in said opening and said opening and said shielding portion are supported by a bridge, and the width of said bridge is narrower than the width of said shielding portion.

12. A scanning electron microscope for imaging by a detected signal, comprising:

an electron illumination system for focusing an accelerated electron beam and illuminating said electron beam to a specimen on a specimen holder;

an electron scanning system for scanning said electron beam on said specimen holder; and an electron detector for detecting an electron beam from said specimen, wherein said microscope has a first limiting aperture and a second limiting aperture between said specimen holder and said electron detector, and includes a portion which controls positions of said first limiting aperture and said second limiting aperture.

* * * * *